United States Patent
Pipkin et al.

(10) Patent No.: US 10,668,160 B2
(45) Date of Patent: *Jun. 2, 2020

(54) DPI FORMULATION CONTAINING SULFOALKYL ETHER CYCLODEXTRIN

(75) Inventors: James D. Pipkin, Lawrence, KS (US); Gerold L. Mosher, Kansas City, MO (US); Douglas B. Hecker, Liberty, MO (US)

(73) Assignee: CyDex Pharmaceuticals, Inc., San Diego, CA (US)

(*) Notice: Subject to any disclaimer, the term of this patent is extended or adjusted under 35 U.S.C. 154(b) by 800 days.

This patent is subject to a terminal disclaimer.

(21) Appl. No.: 13/335,780

(22) Filed: Dec. 22, 2011

(65) Prior Publication Data

US 2012/0164184 A1    Jun. 28, 2012

Related U.S. Application Data

(63) Continuation of application No. 11/550,976, filed on Oct. 19, 2006, now Pat. No. 8,114,438, which is a continuation of application No. PCT/US2005/014010, filed on Apr. 22, 2005.

(60) Provisional application No. 60/564,892, filed on Apr. 23, 2004.

(51) Int. Cl.
| | |
|---|---|
| *A61K 9/16* | (2006.01) |
| *A61P 29/00* | (2006.01) |
| *B32B 5/16* | (2006.01) |
| *A61P 11/00* | (2006.01) |
| *A61K 47/40* | (2006.01) |
| *A61K 9/00* | (2006.01) |

(52) U.S. Cl.
CPC ............ *A61K 47/40* (2013.01); *A61K 9/0075* (2013.01); *Y10T 428/2982* (2015.01)

(58) Field of Classification Search
None
See application file for complete search history.

(56) References Cited

U.S. PATENT DOCUMENTS

| | | |
|---|---|---|
| 3,426,011 A | 2/1969 | Parmerter et al. |
| 4,199,578 A | 4/1980 | Stevenson |
| 4,738,923 A | 4/1988 | Ammeraal |
| 4,920,214 A | 4/1990 | Friedman |
| 4,946,654 A | 8/1990 | Uhlemann et al. |
| 5,024,998 A | 6/1991 | Bodor |
| 5,134,127 A | 7/1992 | Stella et al. |
| 5,241,059 A | 8/1993 | Yoshinaga |
| 5,284,133 A | 2/1994 | Burns et al. |
| 5,324,718 A | 6/1994 | Loftsson |
| 5,376,645 A | 12/1994 | Stella et al. |
| 5,393,880 A | 2/1995 | Shieh et al. |
| 5,437,271 A | 8/1995 | Hodson et al. |
| 5,469,843 A | 11/1995 | Hodson |
| 5,472,954 A | 12/1995 | Loftsson |
| 5,482,032 A | 1/1996 | Smith et al. |
| 5,518,998 A | 5/1996 | Bäckström et al. |
| 5,525,623 A | 6/1996 | Spear et al. |
| 5,569,756 A | 10/1996 | Qi et al. |
| 5,654,276 A | 8/1997 | Barrett et al. |
| 5,658,878 A | 8/1997 | Bäckström et al. |
| 5,668,110 A | 9/1997 | Barrett et al. |
| 5,674,854 A | 10/1997 | Bodley et al. |
| 5,677,280 A | 10/1997 | Barrett et al. |
| 5,683,983 A | 11/1997 | Barrett et al. |
| 5,691,336 A | 11/1997 | Dorn et al. |
| 5,724,959 A | 3/1998 | McAughey et al. |
| 5,750,549 A | 5/1998 | Caldwell et al. |
| 5,756,483 A | 5/1998 | Merkus |
| 5,756,484 A | 5/1998 | Fuertes et al. |
| 5,780,467 A | 7/1998 | Dorn et al. |
| 5,824,668 A | 10/1998 | Rubinfeld et al. |
| 5,846,954 A | 12/1998 | Jouillé et al. |
| 5,863,554 A | 1/1999 | Illum |
| 5,874,418 A * | 2/1999 | Stella et al. ............... 514/58 |

(Continued)

FOREIGN PATENT DOCUMENTS

| | | |
|---|---|---|
| EP | 0 579 435 | 1/1994 |
| EP | 0 392 608 B1 | 6/1995 |

(Continued)

OTHER PUBLICATIONS

Abdullah et al., 1999, The use of bulk density measurements as flowability indicators, Powder Technology, 102:151-165.

Banks et al., 1991, Fluidised-bed granulation: a chronology, Drug Development and Industrial Pharmacy, 17(11):1437-1463.

Broadhead et al., 1992, The spray drying of pharmaceuticals, Drug Development and Industrial Pharmacy, 18(11-12):1169-1206.

Gereg et al., 2002, Roller compaction feasibility for new drug candidates: laboratory to production scale, Pharmaceutical Technology, pp. 14-23.

(Continued)

*Primary Examiner* — Erin E Hirt
(74) *Attorney, Agent, or Firm* — Knobbe, Martens, Olson & Bear LLP

(57) ABSTRACT

An inhalable dry powder formulation containing SAE-CD and an active agent is provided. The formulation is adapted for administration by DPI. The SAE-CD serves as a carrier rather than as an absorption enhancer. The average particle size of the SAE-CD is large enough to preclude (for the most part) pulmonary deposition thereof. Following release from the DPI device, the SAE-CD-containing particles dissociate from the active agent-containing particles in the buccal cavity or throat, after which the active agent-containing particles continue deeper into the respiratory tract. The physicochemical and morphological properties of the SAE-CD are easily modified to permit optimization of active agent and carrier interactions. Drugs having a positive, neutral or negative electrostatic charge can be delivered by DPI when SAE-CD is used as a carrier.

14 Claims, 1 Drawing Sheet

(56) References Cited

U.S. PATENT DOCUMENTS

| | | |
|---|---|---|
| 5,875,776 A | 3/1999 | Vaghefi |
| 5,877,191 A | 3/1999 | Caldwell et al. |
| 5,929,094 A | 7/1999 | Durette et al. |
| 5,935,939 A | 8/1999 | Kararli et al. |
| 5,935,940 A | 8/1999 | Weisz |
| 5,935,941 A | 8/1999 | Pitha |
| 5,942,251 A | 8/1999 | Merkus |
| 5,952,008 A | 9/1999 | Bäckström et al. |
| 5,955,454 A | 9/1999 | Merkus |
| 5,977,070 A | 11/1999 | Piazza et al. |
| 5,988,163 A | 11/1999 | Casper et al. |
| 6,003,512 A | 12/1999 | Gerde |
| 6,022,737 A | 2/2000 | Niven et al. |
| 6,046,177 A | 4/2000 | Stella et al. |
| 6,051,256 A | 4/2000 | Platz et al. |
| 6,077,871 A | 6/2000 | Campeta |
| 6,123,936 A * | 9/2000 | Platz et al. ............ 424/85.6 |
| 6,136,603 A | 10/2000 | Dean et al. |
| 6,138,673 A | 10/2000 | Shepherd |
| 6,153,746 A | 11/2000 | Shah et al. |
| 6,209,538 B1 | 4/2001 | Casper et al. |
| 6,258,341 B1 | 7/2001 | Foster et al. |
| 6,306,440 B1 | 10/2001 | Bäckström et al. |
| 6,309,671 B1 | 10/2001 | Foster et al. |
| 6,383,471 B1 | 5/2002 | Chen et al. |
| 6,436,902 B1 | 8/2002 | Bäckström et al. |
| 6,475,467 B1 * | 11/2002 | Keller et al. ............ 424/45 |
| 6,479,049 B1 | 11/2002 | Platz et al. |
| 6,485,706 B1 | 11/2002 | McCoy et al. |
| 6,495,120 B2 | 12/2002 | McCoy et al. |
| 6,518,239 B1 | 2/2003 | Kuo et al. |
| 6,555,139 B2 | 4/2003 | Sharma |
| 6,559,122 B1 | 5/2003 | Oeswein et al. |
| 6,565,885 B1 | 5/2003 | Tarara et al. |
| 6,582,728 B1 | 6/2003 | Platz et al. |
| 6,589,560 B2 | 7/2003 | Foster et al. |
| 6,599,535 B2 | 7/2003 | Guitard et al. |
| 6,645,466 B1 | 11/2003 | Keller et al. |
| 6,673,335 B1 | 1/2004 | Platz et al. |
| 7,034,013 B2 | 4/2006 | Thompson et al. |
| 7,625,878 B2 * | 12/2009 | Stella et al. ............ 514/58 |
| 7,629,331 B2 | 12/2009 | Pipkin et al. |
| 7,635,773 B2 | 12/2009 | Antle |
| 8,049,003 B2 | 11/2011 | Pipkin et al. |
| 8,114,438 B2 | 2/2012 | Pipkin et al. |
| 8,182,791 B2 * | 5/2012 | Staniforth et al. ............ 424/45 |
| 8,829,182 B2 | 9/2014 | Pipkin et al. |
| 2002/0022584 A1 * | 2/2002 | Assmann et al. ............ 510/470 |
| 2002/0035993 A1 * | 3/2002 | Edwards et al. ......... 128/203.15 |
| 2002/0071870 A1 | 6/2002 | Sharma |
| 2002/0117170 A1 | 8/2002 | Platz et al. |
| 2003/0028014 A1 | 2/2003 | Sikorski et al. |
| 2003/0055023 A1 | 3/2003 | Rajewski et al. |
| 2003/0059376 A1 | 3/2003 | Libbey, III et al. |
| 2003/0064928 A1 | 4/2003 | Bäckström et al. |
| 2003/0065167 A1 | 4/2003 | Lis et al. |
| 2003/0129139 A1 | 7/2003 | Batycky et al. |
| 2003/0138403 A1 | 7/2003 | Drustrup |
| 2003/0185764 A1 | 10/2003 | Staniforth et al. |
| 2003/0215512 A1 | 11/2003 | Foster et al. |
| 2003/0216353 A1 | 11/2003 | Mosher et al. |
| 2004/0234479 A1 | 11/2004 | Schleifenbaum et al. |
| 2005/0164986 A1 | 7/2005 | Mosher et al. |
| 2005/0187245 A1 | 8/2005 | Alnabari et al. |
| 2006/0128654 A1 | 6/2006 | Tang et al. |
| 2006/0194762 A1 | 8/2006 | Reer et al. |
| 2007/0175472 A1 | 8/2007 | Pipkin et al. |
| 2008/0075784 A1 | 3/2008 | Friesen et al. |
| 2009/0123540 A1 | 5/2009 | Pipkin et al. |
| 2010/0093663 A1 | 4/2010 | Antle |
| 2012/0136072 A1 | 5/2012 | Pipkin et al. |
| 2013/0197105 A1 | 8/2013 | Pipkin et al. |
| 2015/0050355 A1 | 2/2015 | Pipkin et al. |

FOREIGN PATENT DOCUMENTS

| | | |
|---|---|---|
| EP | 0 663 815 | 3/1999 |
| EP | 0 487 774 | 6/2002 |
| EP | 1 283 035 A2 | 2/2003 |
| EP | 1 348 428 | 10/2003 |
| EP | 1 709 975 | 10/2006 |
| GB | 2 240 337 | 7/1991 |
| JP | 63-115820 | 5/1988 |
| JP | 63-115821 | 5/1988 |
| JP | 5-504783 A | 7/1993 |
| JP | 6-511513 A | 12/1994 |
| JP | 10-504351 A | 4/1998 |
| JP | 11-60610 | 3/1999 |
| JP | 11-60610 A | 3/1999 |
| JP | 11-171760 | 6/1999 |
| JP | 2004-528288 A | 9/2004 |
| KR | 2001-0075063 | 8/2001 |
| WO | WO 91/11172 A1 | 8/1991 |
| WO | WO 94/02518 A1 | 2/1994 |
| WO | WO 96/23485 | 8/1996 |
| WO | WO 98/50077 | 11/1998 |
| WO | WO 95/11666 | 5/1999 |
| WO | WO 99/42111 | 8/1999 |
| WO | WO 00/015262 A1 | 3/2000 |
| WO | WO 00/066206 | 11/2000 |
| WO | WO 01/05429 A2 | 1/2001 |
| WO | WO 01/40316 | 6/2001 |
| WO | WO 01/78694 | 10/2001 |
| WO | WO 01/87278 A1 | 11/2001 |
| WO | WO 02/056883 | 7/2002 |
| WO | WO 02/058735 A1 | 8/2002 |
| WO | WO 03/055511 | 7/2003 |
| WO | WO 03/055512 | 7/2003 |
| WO | WO 03/066031 A1 | 8/2003 |
| WO | WO 03/079885 A2 | 10/2003 |
| WO | WO 2004/017914 A2 | 3/2004 |
| WO | WO 05/004923 | 1/2005 |
| WO | WO 2005/023308 A1 | 3/2005 |
| WO | WO 05/042584 | 5/2005 |
| WO | WO 05/065435 | 7/2005 |
| WO | WO 05/065649 | 7/2005 |

OTHER PUBLICATIONS

Hancock et al., Apr. 2003, The relative densities of pharmaceutical powders, blends, dry granulations, and immediate-release tablets, Pharmaceutical Technology, pp.

Lin et al., 2003, Spray drying drop morphology: experimental study, Aerosol Science and Technology, 37:15-21.

Mathur, Fluid-Bed Dryers, Granulators and Coaters, in Encyclopedia of Pharmaceutical Technology, vol. 6, Swarbrick et al., eds., CRC Press, 1992, pp. 171-195.

Niro Inc., Feb. 2005, Fluid bed drying—fundamentals, 1 p.

Niro Inc., Feb. 2005, Spray drying & agglomeration, 2 pp.

US Pharmacopeia, 2012, (616) Bulk density and tapped density of powders, USP 36:265-268.

Office Action dated Jul. 8, 2009 in U.S. Appl. No. 12/404,174, filed Mar. 13, 2009.

Adjei et al., Feb. 1992, Bioavailablity of leuprolide acetate following nasal and inhalation delivery to rats and healthy humans, Pharm. Res. 9(2):244-249.

Camoes et al., 2000, 27th Proceedings of the International Symposium on Controlled Release of Bioactive Materials, 794-795.

CyDex, 2002, Cyclopedia, 5(1):3.

Fridriksdottir et al., 1997, Formulation and testing of methazolamide cyclodextrin eye drop solutions, Journal of Controlled Release, 44(1):95-99.

Fridriksdottir et al., Jan. 1996, Design and in vivo testing of 17β-estradiol HPβCD sublingual tablets, Die Pharmazie, 51(1):39-42.

Fridriksdottir et al., Mar. 31-Apr. 2, 1996, Solubilization of β-cyclodextrin: the effect of polymers and various drugs on the solubility of β-cyclodextrin, Proceedings of the Eighth International Symposium on Cyclodextrins, eds. Szejtli et al., Budapest, 373-376.

Fukaya et al., 2003, A cyclosporin a/maltosyl-α-cyclodextrin complex for inhalation therapy of asthma, European Respiratory Journal, 22(2):213-219.

(56) References Cited

OTHER PUBLICATIONS

GEA Niro, 2008, Spray Drier Type MSD™ (Multi-Stage Drier)/FSD™ (Fluidized Spray Drier) with integrated fluid bed, Product Brochure, 3 pp., downloaded from http://www.niro,com/niro/cmsdoc.nsf/webdocprint/webb7gmj9x, 3 pp.
Gudmundsdottir et al., Dec. 2001, Intranasal administration of midazolam in a cyclodextrin based formulation: bioavailability and clinical evaluation in humans, Pharmazie, 56(12):963-966.
Jin et al., Mar. 2008, Selected physical and chemical properties of feverfew (tanacetum parthenium) extracts important for forumlated product quality and performance, AAPS PharmSciTech, 9(1):22-30.
Jung et al., 1996, Comparison of γ-cyclodextrin sulfobutyl ether and unmodified γ-cyclodextrin as chiral selectors in capillary electrophoresis, Journal of Chromatography, 755:81-88.
Kinnarinen et al., 2003, Pulmonary deposition of a budesonide/γ-cyclodextrin complex in vitro, Journal of Controlled Release, 90(2):197-205.
Kobayashi et al., Jan. 1996, Pulmonary delivery of salmon calcitonin dry powders containing absorption enhancers in rats, Pharm. Res., 13(1):80-83.
Kristinsson et al., 1996, Dexamethasone-cyclodextrin-polymer co-complexes in aqueous eye drops, Investigative Ophthalmology & Visual Science, 37(6):1199-1203.
Lammers et al., 1971, Properties of cyclodextrins: Part VI. Water-soluble cyclodextrin-derivatives. Preparation and Analysis, Die Starke, 23(5):167-171.
Lammers et al., 1972, Properties of cyclodextrins, Part VIII Determination of the composition of inclusion complexes of hexane and 2,3-dimethylbutane with cyclodextrin derivatives in aqueous solution, Recl. Trav. Chim. Pays-Bas, 91(6):733-753.
Lindley, 1991, Mixing processes for agricultural and food materials: 1. Fundamentals of mixing, J. Agric. Engng Res. 48:153-170.
Loftsson et al., 1994, The effect of polyvinylpyrrolidone and hydroxypropyl methylcellulose on HPβCD complexation of hydrocortisone and its permeability through hairless mouse skin, European Journal of Pharmaceutical Sciences, 2:297-301.
Loftsson et al., 1994, The effect of water-soluble polymers on drug-cyclodextrin complexation, International Journal of Pharmaceutics (Netherlands), 110(2):169-177.
Loftsson et al., 1996, Effects of cyclodextrins and polymers on topical drug delivery to the eye—evaluations in humans, Proceedings of the 23rd International Symposium on Controlled Release of Bioactive Materials, pp. 453-454.
Loftsson et al., 1996, The influence of water-soluble polymers and pH on hydroxypropyl-β-cyclodextrin complexation of drugs, Drug Development and Industrial Pharmacy, 22(5):401-405.
Loftsson et al., 1997, Cyclodextrins as pharmaceutical excipients, Pharm. Technol. Eur. 9(5):26-34.
Loftsson et al., 1997, Enhanced complexation efficiency of cyclodextrins, Pharmaceutical Research, 14(11):S203.
Loftsson et al., 1998, Cyclodextrin solubilization of ETH-615, a zwitterionic drug, Drug Development and Industrial Pharmacy, 24(4):365-370.
Loftsson et al., 1998, The effect of water-soluble polymers on the aqueous solubility and complexing abilities of β-cyclodextrin, International Journal of Pharmaceutics, 163(1-2):115-121.
Loftsson et al., 1999, Methods to enhance the complexation efficiency of cyclodextrins, S.T.P. Pharma Sciences, 9(3):237-242.
Loftsson et al., 2001, Cyclodextrin solubilization of benzodiazepines: formulation of midazolam nasal spray, International Journal of Pharmaceutics, 212(1):29-40.
Loftsson et al., Apr. 11, 1994, The effect of hydroxypropyl methylcellulose on the release of dexamethasone from aqueous 2-hyroxypropyl-β-cyclodextrin formulations, International Journal of Pharmaceutics (Netherlands), 104:181-184.
Loftsson et al., Oct. 1994, Polymer-cyclodextrin-drug complexes, Pharmaceutical Research, 11(10):S225.
Loftsson et al., Oct. 1996, Pharmaceutical applications of cyclodextrins. 1. Drug solubilization and stabilization, Journal of Pharmaceutical Sciences, , 85(10):1017-1025.
Loftsson et al., Sep. 16, 1996, Drug-cyclodextrin-polymer ternary complexes, European Journal of Pharmaceutical Sciences, 4(SUPPL.):S144.
Loftsson et al., Sep. 1996, Solubilization of β-cyclodextrin, Eur. J. Pharm. Sci, 4(Suppl.):S143.
Loftsson et al., Sep. 2001, Sustained drug delivery system based on a cationic polymer and an anionic drug/cyclodextrin complex, Pharmazie, 56(9):746-747.
Loftsson, 1996, Topically effective acetazolamide eye-drop solution in man, Pharmaceutical Sciences, 2(6):277-279.
Loftsson, 1998, Drug-cyclodextrin complexation in the presence of water soluble polymers: enhanced solubility and percutaneous transport, Abstracts of Papers Part 1, 216th ACS National Meeting, Boston, Aug. 23-27, CELL-016.
Loftsson, Apr. 2-6, 1995, The effect of polymers on cyclodextrin complexation, Book of Abstracts, 209th ACS National Meeting, 209(1):33-CELL.
Loftsson, Nov. 1988, Increasing the cyclodextrin complexation of drugs and drug bioavailability through addition of water-soluble polymers, Pharmazie, 53(11):733-740.
Masson et al., 1999, Drug-cyclodextrin complexation in the presence of water-soluble polymers: enhanced solubility and percutaneous transport, ACS Symposium Series, 737 (Polysaccharide Applications), pp. 24-45.
Modified Cyclodextrins: Scaffolds and Templates for Supramolecular Chemistry, Easton et al. eds., Imperial College Press, London, UK, 1999.
Nakate et al., Mar. 2003, Improvement of pulmonary absorption of cyclopeptide FK224 in rats by co-formulating with Eur. J. Pharm. Biopharm., 55(2):147-154.
New Trends in Cyclodextrins and Derivatives, Duchene ed., Editions de Sante, Parks, France, 1991.
Nimbalkar et al., 2001, Activation of diacetyldapsone and a preliminary evaluation of a cyclodextrin-diacetyldapsone complex in cultured lung cells, Biotechnol. Appl. Biochem. 33:123-125.
Poly(ethylene glycol) Chemistry: Biotechnical and Biomedical Applications, Harris et., Plenum Press New York, 1992.
Polymer Science, in Physical Pharmacy. Physical Chemical Principles in Pharmaceutical Sciences, 3rd edition, Martin et al., 1983, pp. 592-638.
Polymers and Macromolecules, in Physicochemical Principles of Pharmacy, 2nd edition, Florence et al., eds. pp. 281-334, 1988.
Qu et al., 2002, Sulfoalkyl ether β-cyclodextrin derivatives: synthesis and characterizations, J. Inclusion Phenom. Macro. Chem, 43:213-221.
Ramachandruni et al., May 2001, Design and validation of an annular shear cell for pharmaceutical powder testing, Journal of Pharmacetuical Sciences, 90(5):531-540.
Remington's Pharmaceutical Sciences, 18th Edition, Gennaro ed., 1990, Hydrophilic Dispersons, pp. 291-294.
Remy, Oct. 2010, Granular flow, segregation and agglomeraion in bladed mixers, dissertation for the degree of Doctor of Philosphy, Graduate Program in Chemical and Biochemical Engineering, Rutgers, The State University of New Jersey, 285 pp.
Rodrigues et al., May 2003, The effect of cyclodextrins on the in vitro and in vivo properties of insulin-loaded (D,L-Lactic-Co-Glycolic Acid) microspheres, Artificial Organs, 27(5):492-497.
Sandler et al., Feb. 2010, Prediction of granule packing and flow behavior based on particle size and shape analysis, Journal of Pharmaceutical Sciences, 99(2):958-968.
Savolainen et al., 1998, Co-administration of a water-soluble polymer increases the usefulness of cyclodextrins in solid oral dosage forms, Pharmaceutical Research, 15(11):1696-1701.
Savolainen et al., May 31-Jun. 3, 1998, Coadministration of a water-soluble polymer increases the usefulness of cyclodextrins in solid oral dosage forms, 9th Proceedings of the International Symposium on Cyclodextrins, Santiago de Comostela, Spain, eds. Labandeira et al., pp. 261-264.
Shao et al., 1994, Cyclodextrins as mucosal absorption promoters of insulin: III. Pulmonary route of delivery, Eur. J. Pharm. Biopharm. 40(5):283-288.
Sigurdardottir et al., Dec. 29, 1995, The effect of polyvinylpyrrolidone on cyclodextrin complexation of hydrocortisone and its

(56) References Cited

OTHER PUBLICATIONS diffusion through hairless mouse skin, International Journal of Pharmaceutics (Netherlands), 126:73-78.
Srichana et al., Jun. 2001, Cyclodextrin as a potential drug carrier in salbutamol dry powder aerosols: the in-vitro deposition and toxicity studies of the complexes, Respiratory Medicine, 96(6):513-519.
Staniforth et al., 1982, Interparticle forces in binary and ternary ordered powder mixes, J. Pharm Pharmacol. 34:141-145.
Tarver et al., 2002, 2-O-substituted cyclodextrins as reversal agents for the neuromuscular blocker rocuronium bromide, Bioorganic & Medicinal Chemistry, 10:1819-1827.
Teunou et al., 1999, Effect of relative humidity and temperature on food powder flowability, Journal of Food Engineering, 42:109-116.
Third European Congress of Pharmaceutical Sciences, Edinburgh, Scotland, UK, Sep. 15-17, 1996.
Van der Kuy et al., Nov. 1999, Bioavailability of intranasal formulations of dihydroergotamine, Eur. J. Clin. Pharmacol., 55(9):667-680.
Williams et al., Mar. 1999, Influence of formulation technique for hydroxypropyl-β-cyclodextrin on the stability of aspirin in HFA 134a, Eur. J. Pharm. Biopharm, 47(2):145-152.
Worth et al., 1997, Steroid/cyclodextrin complexes for pulmonary delivery, Proceedings of the International Symposium on Controlled Release of Bioactive Materials, 24:747-748.
Office Action dated Jul. 21, 2010, in U.S. Appl. No. 11/550,976, Pipkin et al., filed Oct. 19, 2006.
"Captisol," accessed at: http://captisol.ligand.level3.pint.com/captisol-technology/product-advantages/, print date of Feb. 11, 2011, 1 page.
"Fluidized Bed Spray Granulation," Bayer Technology Services, electronic file date of Oct. 2005, 2 pages.
Jain, A., et al., "Hygroscopicity, phase solubility and dissolution of various substituted sulfobutylether β-cyclodextrins(SBE) and danazol-SBE inclusion complexes," Int. J. Pharm. 212:177-186, Elsevier Science Publishers B.V., Netherlands (2001).
Kinnarinen, T., et al., "The in vitro Pulmonary Deposition of a Budesonide/γ-Cyclodextrin Inclusion Complex," J. Inclusion Phenom. Macrocyclic Chem. 44:97-100, Kluwer Academic Publishers, Netherlands (2002).
Kubota, N., "Fluidized bed granulation method," Granulation Handbook, 1$^{st}$ ed., pp. 249-270 (1975).
Luna, E., et al., "Fractionation and characterization of 4-sulfobutyl ether derivatives of cyclomaltoheptaose (β-cyclodextrin)," Carbohydr. Res. 299:103-110, Elsevier Science Publishers B.V., Netherlands (1997).
Matsushita, Y., "Pharmaceutics I, Drug Preparation and Formulation," pp. 59-62 (1995).
Mosher, G. and Thompson, D., "Complexation and Cyclodextrins," Encyclopaedia of Pharmaceutical Technology 19(Suppl. 2):49-88, Informa Healthcare, United Kingdom (2000).
Mueller et al., Proceed. Int'l. Sym. Control. Rel. Bioact. Mater. 24:69-70 (1997).
"Fluid Bed Granulation, Drying, and Coating," accessed at: http://www.niroinc.com/pharma_systems/fluid_bed_drying.asp, print date of Nov. 11, 2011, 3 pages.
Nachaegari, S., et al., "Coprocessed Excipients for Solid Dosage Forms," Pharmaceutical Technology, pp. 52-64, Advanstar Communications, Inc., United States (Jan. 2004).
Nakate, T., et al., "Comparison of the lung absorption of FK224 inhaled from a pressurized metered dose inhaler and a dry powder inhaler by healthy volunteers," Eur. J. Pharm. Biopharm. 56:319-325, Elsevier Science Publishers B.V., Netherlands (Nov. 2003).
Pinto, J. and Marques, H., "Beclomethasone/cyclodextrin inclusion complex for dry powder inhalation," STP-Pharma Sciences 9:253-256, Editions de Santé, France (1999).
Rajewski, R. and Stella, V., "Pharmaceutical applications of cyclodextrins. 2. in vivo drug delivery," J. Pharm. Sci. 85:1142-1169, Wiley, United States (1996).
Smyth, H., et al., "Dynamic Electrostatic Charge Determinations of Dry Powder Blends for Inhalation: Correlations with Dispersion Performance," Respiratory Drug Delivery IX, pp. 805-808, Respiratory Drug Delivery Online, United States (Apr. 2004).
Smyth, H., et al., "Influence of Physical Form of Captiosol® Particles on Performance as a Dry Powder Aerosol Carrier," Respiratory Drug Delivery IX, pp. 809-812, Respiratory Drug Delivery Online, United States (Apr. 2004).
Stella, V. J., "SBE7-β-CD, A New, Novel and Safe Polyanionic β-Cyclodextrin Derivative: Characterization and Biomedical Applications," in Proceedings of the Eighth International Symposium on Cyclodextrins, Budapest, Hungary, Mar. 31-Apr. 2, 1996, Szejtli, J., and Szente, L., eds., Kluwer Academic Publishers, Dordrecht, Netherlands, pp. 471-476, (1996).
Szente, L. and Szejtli, J., "Highly soluble cyclodextrin derivatives: chemistry, properties, and trends in development," Adv. Drug Deliv. Rev. 36:17-28, Elsevier Science Publishers, B.V., United Kingdom (1999).
Tötterman, A., et al., "Intestinal safety of water-soluble β-cyclodextrins in paediatric oral solutions of spironolactone: effects on human intestinal epithelial Caco-2 cells," J. Pharm. Pharmacol. 49:43-48, Wiley, United Kingdom (1997).
Vozone, C. and Marques, H., "Complexation of Budesonide in Cyclodextrins and Particle Aerodynamic Characterization of the Complex Solid Form for Dry Powder Inhalation," J. Inclusion Phenom. Macrocyclic Chem. 44:111-115, Kluwer Academic Publishers, Netherlands (Dec. 2002).
Accelerated Examination Support Document filed Jan. 31, 2009, in U.S. Appl. No. 12/363,719, Pipkin et al., filed Jan. 31, 2009.
Supplemental Accelerated Examination Support Document filed Sep. 11, 2009, in U.S. Appl. No. 12/363,719, Pipkin et al., filed Jan. 31, 2009.
Notice of opposition to a European patent, submitted by Strawman Limited in the Opposition to European Patent No. 1945228, dated Jan. 5, 2012, 17 pages.
International Search Report for International Application No. PCT/US2005/38933, filed on Oct. 26, 2005, dated Aug. 3, 2006, U.S. Patent Office, Alexandria, VA, USA.
International Search Report for International Application No. PCT/US2005/014010, filed on Apr. 22, 2005, dated Apr. 19, 2007, U.S. Patent Office, Alexandria, VA, USA.
Examiner's First Report in Australian Application No. 2005237523, dated Sep. 16, 2008, Australian Patent Office, Australia.
Supplementary European Search Report for European Application No. 05743067.0, dated Mar. 18, 2010, European Patent Office, Munich, Germany.
Official Action in Russian Application No. 2006141358, dated Feb. 3, 2009, Patent Office of the Russian Federation, Russia.
Unverified English language translation of Official Action in Russian Application No. 2006141358, dated Feb. 3, 2009, Patent Office of the Russian Federation, Russia.
Office Action dated Sep. 10, 2010, in U.S. Appl. No. 12/108,228, Pipkin, J., et al., filed Apr. 23, 2008.
Office Action dated May 15, 2009, in U.S. Appl. No. 12/363,719, Pipkin, J., et al., filed Jan. 31, 2009.
English language translation of pp. 253 and 268 of Kubota, N., "Fluidized bed granulation method," Granulation Handbook, 1$^{st}$ ed., pp. 249-270 (1975).
English language translation of pp. 60 and 61 of Matsushita Y., "Pharmaceutics I, Drug Preparation and Formulation," pp. 59-62 (1995).
Office Action dated Jul. 21, 2010, in U.S. Appl. No. 11/550,976, Pipkin, J., et al., filed Oct. 19, 2006.
Office Action dated Dec. 2, 2010, in U.S. Appl. No. 11/550,976, Pipkin, J., et al., filed Oct. 19, 2006.
Submission in opposition proceedings, submitted by CyDex Pharmaceuticals, Inc. in the Opposition to European Patent No. 1945228, dated Aug. 23, 2012, 30 pages.
GEA Niro, 2014, Fluidized spray dryer FSD™ from GEA Niro, http://www.niro.com.niro.cmsdoc.nsf/WebDoc/ndkk5hmchfFluidizedSprayDryer, 3 pp.
GEA Niro, 2014, The MSD™ Multi-State Dryer for the Dairy Industry, http://www.niro.com/niro/cmsdoc.nsf/webdoc/webb7gmj9x, 3 pp.

(56) References Cited

OTHER PUBLICATIONS

GEA Niro, FSD-Granulator™: improved agglomeration for precise control of essential product quality and characteristics, 4 pp., downloaded from the internet on Feb. 25, 2014.

GEA Niro, Spray drying solutions for R&D and small-scale production, 16 pp., downloaded from the internet on Feb. 25, 2014.

Jain et al., Jan. 1, 2001, Hygroscopicity, phase solubility and dissolution of various sulfobutylether beta-cyclodextrins and danasol-SBE inclusion complexes, International Journal of Pharmaceutics, 212(2):177-186.

Li et al., 2004, Interparticle van der Waals force in powder flowability and compactibility, International Journal of Pharmaceutics, 280:77-93.

Polymer Science, in Physical Pharmacy. Physical Chemical Principles in Pharmaceutical Sciences, 4th edition, Martin et al., Lippincott Willliams & Wilkins, Baltimore, MD, 1993, pp. 446-450.

Ridgway et al., May 1, 1969, The effect of particle shape on powder properties, J. Pharm. Pharmac. 21, Suppl., pp. 30S-39S.

Sulfobutylether β-Cyclodextrin, in Pharmaceutical Excipients 2004: Single-user version, Rowe et al., eds., Pharmaceutical Press and American Pharmacists Association, 21 pp.

Thalberg et al., 2004, Comparison of different flowability tests for powders for inhalation, Powder Technology, 146:206-213.

United States Pharmacopeia, Jan. 1, 2005, (616) Bulk Density and Tapped Density, pp. 2379-2380.

Verhing, May 2008, Pharmacaceutical particle engineering via spray drying, Pharmaceutical Research, 25(5):999-1022.

Office Action dated Mar. 24, 2015 in U.S. Appl. No. 13/794,652.

Extended European Search Report dated Feb. 17, 2014 in European Application No. 13184888.9.

Crowder et al., 2003, Chapter 5. Behavior of Particles, in a Guide to Pharmaceutical Particulate Science, Interpham/CRC, Boca Raton, Florida, pp. 77-121.

Maggi et al., 1999, Influence of the moisture on the performance of a new dry powder inhaler, International Journal of Pharmaceutics, 177:83-91.

PharmaSys Pharmaceutical Systems, Feb. 1, 2001, Spray Drying, http://www.pharmasys.pe.kr/sd.htm, 12 pp.

Sulfobutylether β-Cyclodextrin, in Handbook of Pharmaceutical Excipients, 6th Edition, 2009, Rowe et al., eds., Pharmaecutical Press, Grayslake, IL, pp. 714-717.

Office Action dated Sep. 28, 2015 in U.S. Appl. No. 13/794,652.

Office Action dated Oct. 5, 2015 in Korean patent application No. 10-2012-7011393.

Excipient Guide, 2016, http://www.excipientsguide.com/excipient_details.aspx?Id+245, 2 pp.

CyDex Home Page, Innovative Drug Delivery Technologies, http://web.archive.org/web/20030622192941/http://www.captisol.com/, Jun. 22, 2003, 1 p.

Office Action dated May 5, 2016 in U.S. Appl. No. 13/794,652.

Sotthivirat et al., 2000, Flow and tabletting properties of $(SBE)_{7m}$-β-CD, 10th ICS, Ann Arbor, 6 pp.

Office Action dated Nov. 30, 2016 in U.S. Appl. No. 13/794,652.

\* cited by examiner

DPI FORMULATION CONTAINING SULFOALKYL ETHER CYCLODEXTRIN

CROSS-REFERENCE TO EARLIER FILED APPLICATIONS

This application is a continuation of U.S. application. Ser. No. 11/550,976, filed Oct. 19, 2006, now U.S. Pat. No. 8,114,438, which is a continuation of International Appl. No. PCT/US2005/014010, filed Apr. 22, 2005, which claims the benefit of U.S. Appl. No. 60/564,892, filed Apr. 23, 2004, the entire disclosure of each of which is hereby incorporated by reference.

FIELD OF THE INVENTION

The present invention relates to a method of administering, and a dry powder formulation for administering an inhalable active agent by inhalation with a dry powder inhaler (DPI) using sulfoalkyl ether cyclodextrin as a carrier therefor. The invention also relates to methods of treating diseases and disorders of the lung by administration of a dry powder comprising therapeutic agent and SAE-CD as a carrier.

BACKGROUND OF THE INVENTION

The delivery of a drug by inhalation allows deposition of the drug in different sections of the respiratory tract, e.g., throat, trachea, bronchi and alveoli. Generally, the smaller the particle size, the longer the particle will remain suspended in air and the farther down the respiratory tract the drug can be delivered. Drugs are delivered by inhalation using a nebulizer, metered dose inhaler (MDI), or dry powder inhaler (DPI).

Dry powder inhalers provide powder pharmaceuticals in aerosol form to patients. In order to generate an aerosol, the powder in its static state must be fluidized and entrained into the patient's inspiratory airflow. The powder is subject to numerous cohesive and adhesive forces that must be overcome if it is to be dispersed. Fluidization and entrainment requires the input of energy to the static powder bed.

DPIs can be divided into two classes: passive and active devices. Passive devices rely solely upon the patients inspiratory flow through the DPI to provide the energy needed for dispersion. This method has the advantage that drug release is automatically coordinated with the patient's inhalation. The disadvantage is that dispersion is typically highly dependent on the patient's ability to inhale at an optimum flow rate for aerosol generation. Depending on the inhaler design, this requirement may be difficult for some patients if the device resistance to airflow is high. Active dispersion devices have been under development for the past ten years but none has yet been approved. Like propellant driven metered dose inhalers, active devices use a source external to the patient to provide the energy needed for powder dispersion. This has the advantage of potentially reducing the dependence of uniform dosing on the patient's capabilities. However, without a feedback mechanism for the energy source, it is still possible that different patients will receive different doses. In addition, the complexity of these devices has contributed to their inability to achieve regulatory approval and may increase the cost of the device.

Passive devices have progressed in their complexity and performance since the introduction of the Allen & Hanbury's Rotahaler and the Fison's Spinhaler in the 1970's. Passive dispersion relies on the airflow generated by the user to aerosolize the powdered drug. All passive devices disperse the drug by passing the airflow through the powder bed. Early devices dispersed very small quantities of respirable sized particles, often on the order of 10% of the nominal dose. In general, this poor performance can be attributed to the incomplete deaggregation of smaller drug particles from larger carrier particles used as a diluent and an aid to powder flow during dispersion. Modern devices utilize significant turbulence to aid in the deaggregation process. Turbulence can be provided by tortuous flow paths for the particle laden airflow as in the AstraZeneca Turbuhaler, the Schering-Plough Twisthaler and U.S. Pat. No. 5,469,843; changing dimensions of the airflow path (U.S. Pat. No. 5,437,271); or by impactor plates that also reduce the emission of large particles (U.S. Pat. No. 5,724,959). A device developed by Innovative Devices (U.S. Pat. Nos. 6,209,538 and 5,988,163) addresses the desirability of dispersing powder at optimal flow rates via channels whose operation is flow dependent. Initially, flow is diverted around the drug and is allowed to pass through the drug only when the optimal flow rate has been obtained. This device bridges the gap between passive and active devices by adding active features to a passive device.

Active devices use mechanisms such as springs or a battery to store energy that can be released to aid in powder dispersion. The best known active devices are the Inhale (Nektar) Deep Lung delivery system and the Dura Spiros. The Inhale device uses compressed air generated by the user through a spring loaded pump mechanism to disperse powder drug. There are a few other patents identified that utilize compressed air (U.S. Pat. Nos. 5,875,776 and 6,003,512) or a vacuum (U.S. Pat. No. 6,138,673) to provide energy for dispersion. The Dura Spiros DPI uses a battery driven impeller to disperse drug powder. The impeller operates only when the patient inhales through the DPI to ensure that dosing does not occur when not in use. U.S. Pat. Nos. 5,469,843 and 5,482,032 describe another mechanism of dispersion (use of a hammer or other means of impaction to dislodge drug from a powder bed typically contained on a blister strip). Little published data is available for the active devices since most of their development has occurred in a proprietary atmosphere. Some of the patented technology, both for active and passive devices, is only conceptual.

For lung deposition, drug particles are generally required to be smaller than 10 μm (microns) in aerodynamic diameter. They may be prepared by either size reduction methods, such as milling, or particle construction methods, such as condensation, evaporation or precipitation. Historically, respirable particles are produced by jet-milling, where there is little control over the particle size, shape or morphology. The resulting fractured particles are highly electrostatic, cohesive, and subjective to changes in crystallinity. Alternative methods of particle generation include spray-drying, solvent evaporation or extraction or supercritical fluid condensation. All of these methods produce structurally more uniform particles.

Particles smaller than 10 μm generally exhibit poor flow properties due to their high interparticle forces. Formulation strategies to improve the flowability of respirable particles include the controlled agglomeration of drug particles or adhesion onto excipient carrier particles in the form of interactive mixtures. The agglomerates or interactive mixtures are required to be strong enough to withstand processing, storage or transport processes, but weak enough to allow drug deaggregation and dispersion during actuation. Controlled agglomeration may be achieved by feeding micronized powders through a screw feeder, followed by spheronization in a rotating pan or drum. This method may be used for formulations containing drug alone or drug/lactose blends. Factors affecting the aerosol dispersion of carrier-based formulations include drug and carrier properties, such as size, shape, surface roughness (rugosity), chemical composition and crystalline state, the drug-carrier ratio and the presence of ternary components.

The drug particle size effects aerosol dispersion. Different sized spray-dried mannitol (2.7 to 7.3 µm) and disodium cromoglycate (2.3 to 5.2 µm) particles were examined. Higher aerosol dispersion, due to less cohesion, was observed in larger particles; however, lower fine particle fraction (FPF) was produced due to greater impaction on the throat and upper stages of the impinger and smaller proportion of fine particles. Conditioning or surface modification of drug particles may reduce aggregation and improve aerosol dispersion. The amorphous content of particles may be reduced by treatment with water vapor in controlled temperature and relative humidity conditions or treatment in a vacuum oven. Surface modification by adhesion of nanoparticles onto the drug particles may increase aerosol dispersion. Hydrophilic silicic acid and hydroxypropylmethylcellulose phthalate (HPMCP) nanoparticles increased device emission and respirable fractions of pranlukast hydrate in both drug alone and carrier-based formulations.

Conflicting reports exist on the influence of drug concentration in carrier-based DPI formulations. Increasing drug concentration may increase the respirable fraction or reduce the respirable fraction.

The particle size, shape, surface morphology and chemical composition of carrier particles can influence aerosol dispersion. Increased drug dispersion and deposition is generally observed with smaller carrier size and increased proportion of fine particles. However, the carrier size did not affect the FPF in some formulations. Higher FPF was produced with larger carrier sizes (within 63-90 µm). Poor dispersion of nedocromil was obtained using coarse carrier systems, whereas the use of fine carrier particles and high shear mixing techniques physically disrupted the drug-drug contacts and promoted deaggregation. Elongated carriers increased aerosol dispersibility and drug FPF, possibly due to increased duration in the airstream drag forces. Carriers with smooth surfaces produced higher respirable fractions. Low respirable fractions were obtained from carriers with macroscopic surface roughness or smooth surfaces, whereas high respirable fractions were obtained from carriers with microscopic surface roughness, where smaller contact area and reduced drug adhesion occurred at the tiny surface protrusions. A modification of carrier formulation involves the use of soft friable lactose pellets containing micronized lactose particles, which break down into primary particles during inhalation has also been described. The lactose pellet may be coated with drug. In another study, carrier particles with good powder flow characteristics exhibited reduced adhesion to a defined solid surface and produced higher drug deposition in an animal model. The influence of carrier particle size on the performance of a formulation in a DPI device is summarized in the following table.

| Property | Improved by |
| --- | --- |
| Uniformity and blending | Increasing particle size |
| Powder flow | Increasing particle size |
| Entrainment tendancy | Increasing particle size (typically, but depends on properties of carrier) |
| Dispersion and Potential for Lung Delivery | Decreasing particle size (function of drug-carrier and aggregate particle size) |

Thus for dry powder inhaler formulations, the size of carrier particles should be selected on the basis of a balance between, these interrelated performance characteristics. Specifically, inter-particulate forces should be such that the drug particles adhere to the carrier (to aid in blending, uniformity, and allow the entrainment of drug into the inspiratory air-stream), yet also allow detachment of the fine drug particles from the surface of the coarser carrier particles so that delivery to the lung can be facilitated.

In vitro drug deposition has been examined using different grades of lactose carrier. The higher FPF of salbutamol (albuterol) sulphate obtained from anhydrous and medium lactose was attributed to a higher proportion of fine particles and smooth surface roughness. The higher FPF of nacystelyn obtained from anhydrous β-lactose was attributed to its intermediate surface roughness. Other sugars were investigated as fine and coarse carriers. Higher FPF was obtained using mannitol coarse carrier, possibly due to a higher fine particle content and more elongated shape. Mixtures with added fine particle carrier produced higher FPF with little difference observed between the fine carrier type.

The addition of fine ternary components has increased the FPF of various drug particles. Ternary components examined include magnesium stearate, lactose, L-leucine, PEG 6000 and lecithin. Many possible explanations exist for the mechanism of action of ternary components, including the saturation of active sites on the carrier, electrostatic interactions and drug redistribution on the ternary component.

Recent developments in the improvement of DPI formulation efficiency are focused on particle engineering techniques. Improved aerosol dispersion of particles may be achieved by the co-spray-drying with excipients, such as sodium chloride, or human serum albumin (HSA). Respirable-sized particles composed of hydrophobic drug and hydrophilic excipients were produced by simultaneous spray-drying of separate solutions through a co-axial nozzle. Therapeutically active peptide particles have been produced by spray-drying with good flow and dispersibility properties, including insulin, α-1-antitrypsin and β-interferon. The addition of stabilizing excipients, such as mannitol and human serum albumin (HSA) is generally required. Spray-dried microspheres composed of cellulose lower alkyl ethers, such as hydroxypropyl methyl cellulose, may be used for sustained drug release. These particles are adhesive following water adsorption from the lung mucosa. Stable dry powder formulations of polynucleotide complexes were produced by lyophilization with a cryoprotectant, such as mannitol, followed by sieving or milling.

Large porous particles (geometric diameters of 5-30 µm and tap density less than 0.4 g/mL) with aerodynamic diameters of 1-5 µm are prepared by spray-drying. These large particles are less cohesive, due, to reduced van der Waals forces, and have improved flow and aerosol dispersion properties. Increased rough surface texture may further minimize particle aggregation and improve flow. Particles deposited in the alveolar regions may avoid phagocytic engulfment by size exclusion. Controlled rate of drug release is achieved using biodegradable polymers, such as poly(lactic acid) (PLA) and poly(glycolic acid) (PGA).

Surfactants, such as dipalmitoyl phosphatidylcholine (DPPC) may be incorporated to further improve powder flow, aerosol dispersion and lung deposition.

Drug or peptide encapsulated in hollow microcapsules are free flowing, easily deaggregated and produce high respirable fractions. Wall materials include human serum albumin (HSA) or PGA and PLA. Reduced dissolution may be obtained by coating with fatty acids, such as palmitic acid or lipid soluble surfactants, such as Span 85. The PulmoSphere™ small hollow particles (5 μm geometric diameter and bulk densities less than 0.1 g/mL) are spray-dried from emulsions of drug, phosphatidylcholine and perfluorocarbon.

Current commerical DPI formulations are based on drug agglomerates or carrier-based interactive mixtures. Excipients act as diluents and stablility enhancers and improve flowability and aerosol dispersibility. Since lactose is the only US-approved excipient for DPI formulations, there is a need for alternative safe excipients. Suggestions have included carbohydrates, such as fructose, glucose, galactose, sucrose, trehalose, raffinose, melezitose; alditols, such as mannitol and xylitol; maltodextrins, dextrans, cyclodextrins, amino acids, such as glycine, arginine, lysine, aspartic acid, glutamic acid and polypeptides, such as human serum albumin and gelatin. To mask the unpleasant taste of some inhaled drug compounds, flavoring particles containing maltodextrin and peppermint oil may be incorporated into dry powder formulations. Large sized particles increase mouth deposition and reduce lung deposition.

Commercial formulations predominantly deliver bronchodilators, anticholinergics and corticosteriods for the local treatment of asthma and chronic airways obstruction. New formulations contain multiple drug components, such as fluticasone and salmeterol. This brings about further complications in the particle interactions involved with powder systems. There has been much speculation on the potential delivery of locally and systemically acting drugs such as analgesics (fentanyl and morphine), antibiotics, peptides (insulin, vasopressin, growth hormone, calcitonin, parathyroid hormone), RNA/DNA fragments for gene therapy and vaccines. However, the only new therapy provided using DPI formulations is zanamivir (Relenza), which is mainly targeted at the upper respiratory tract for the treatment of influenza.

The use of formulation additives to enhance drug uptake has also been considered. The nature of these absorption promoters is based on a variety of mechanisms, not all of which are fully elucidated. The best known are the classical absorption enhancers such as bile salts and surfactants which are known to disrupt cell membranes and open tight junctions rendering epithelia more permeable. This has been followed by the use of small particulates containing drug, which may find their way across epithelia intact. Many of these particulate approaches have yet to be published with respect to lung delivery but some of the companies with relevant technology include Nanosystems, PDC and BioSante. An alternative approach involves the close association of a carrier molecule with peptides and proteins for transport across the epithelium. The mechanism of improved uptake is not fully characterized for these molecules with respect to the lung epithelium. The maximum doses that can be delivered to the lungs limit the systemic delivery of drugs. However, the potential advantage of all of the particulate or molecular transport promoters is that they may improve bioavailability of the drug, maximizing the proportion of the dose that reaches the site of action. This is particularly important for macromolecules which may not be delivered effectively by any other route of administration. The safety implications of using any agent that modifies the physiology of the lung must be fully considered if it is to be adopted for any commercially viable product.

The principle advantages of a DPI and MDI over a nebulizer are that very low volumes of a formulation can be used thereby making feasible the manufacture and use of small delivery devices. Moreover, DPI and MDI devices require very short administration times as compared to nebulizers. MDI devices, however, are becoming less acceptable due to the international restrictions on the use of chlorofluorocarbon propellants that are required for operation of an MDI.

The administration of these drugs in the form of micronized powder requires the use of suitable dry powder inhalers (DPIs).

DPIs in turn can be divided into two additional basic types:

single dose inhalers, for the administration of single subdivided doses of the active compound;

multidose dry powder inhalers (MDPIs), preloaded with quantities of active principles sufficient for longer treatment cycles.

Although micronization of the drug particles is essential for penetration to the deepest branchings of the pulmonary tree during inhalation, it is also known that the finer are the particles, the stronger are the cohesion forces. In multidose inhalers, said effects hamper the loading of the doses of powder from the reservoir system to the aerosolization chamber, since the cohesion forces reduce free flowing of the particles and promote their agglomeration and/or their adhesion to the walls. The aforementioned effects therefore impair the efficiency and reproducibility of the delivered dose and are detrimental to the respirable fraction.

Multidose inhalers work properly when so-called freeflowing powders are used, generally formulated by mixing the micronized drug with a carrier material (generally lactose, preferably α-lactose monohydrate) consisting of coarser particles, approximately equal or greater than 100 microns. In such mixtures, the micronized active particles mainly adhere to the surface of the carrier particles whilst in the inhaler device; on the contrary, during inhalation, a redispersion of the drug particles from the surface of the carrier particles occurs allowing the formers to reach the absorption site into the lungs.

Mixing with the carrier also facilitate the introduction and withdrawal of the inhalation preparation, in a regular dose, from the reservoir of a multidose inhaler or its dosage in single-dose containers. Mixing of the micronized drug with the coarse carrier therefore leads to the production of a mixture in which the micronized drug is distributed uniformly on the carrier particles as a result of the interactions, usually of an electrostatic nature, which establish between the drug particles and the carrier particles.

Said interactions lead to the production of a so-called ordered mixture. It is extremely important for the interactions to be weak and reversible, so that, since transport in the air stream and the respirability of the powder depend on the particle size, only the micronized drug particles will be able to be deposited in the lungs, whereas the coarser carrier particles will be deposited, because of their mass, in the upper airways. Due to the weak interactions between the two components of the mixture, breathing-in through the inhaler causes separation of the micronized drug particles from the coarse carrier particles and therefore inhalation of the smaller particles and deposition of the coarser particles in the oropharyngeal cavity. Accordingly, it is of great applicative interest to find new carriers for inhalers and new techniques for the production of drug-carrier mixtures that are easy to handle and able to generate a high respirable fraction.

The use of a carrier is indeed not free of drawbacks in that the strong interparticle forces between the two ingredients may prevent the separation of the micronized drug particles from the surface of the coarse carriers ones on inhalation, so compromising the availability of the drug to the respiratory tract.

In the prior art there are many examples of processes for modifying the surface conditions of the carrier with the aim of reducing the strength of the interactions between the particles during inhalation, without causing pre-separation of the drug particles in the inhaler.

Ganderton (GB 2 240 337) reports that the surface conditions of the particles, in particular their rugosity, are critical for the behavior of the carrier during inhalation and claims pharmaceutical carriers, such as lactose, consisting of particles whose rugosity is controlled by a crystallization process. The rugosity of the said particles is evaluated using measurements of surface area, based on gas permeametry. The surface area value measured by this technique, relative to the theoretical surface area value, provides a numerical index of rugosity called Ganderton scale.

Staniforth (WO 95/11666) claims a milling process preferably carried out in a ball mill, called corrasion (for analogy with the effect of wind on rocks), which alters the surface characteristics of the carrier by removing asperities in the form of small grains; these grains in turn can become attached to the clefts of the surface area of the particles, so saturating the high energy sites. As a result of this preliminary treatment of the carrier, the micronized drug particles are deposited preferentially on lower-energy sites and so are subject to weaker forces of interparticle adhesion.

On the other hand, the operation of some multidose inhalers requires the use of optimum carriers of high flowability, a characteristic that can only be imparted by using particles with a greater'granulometric distribution.

Disaggregation of the active principle from the carrier during inhalation can also be made more efficient by addition of a fraction of fine particles of the same carrier. The Boheringer patent EP 0 663 815 claims the use of carriers for controlling and optimizing the amount of drug released during the aerosolization phase, comprising suitable mixtures of coarse particles with size>20 microns and of fine particles with size<10 microns.

Finally, in the prior art, additives with lubricant, glidant or anti-adherent properties, dry-mixed with the carrier, have been employed with the aim of reducing the forces of attraction between drug and carrier. For example, mixing of magnesium stearate with crystalline lactose is able to reduce the forces of adhesion between drug and carrier, when this mixture is used as inhalation carrier. For explaining the effectiveness of magnesium stearate in the aerosolization of inhalation powders, investigations conducted on powder mixtures for tablets cap be taken into account (Staniforth et al., J. Pharm. Pharmacol. 1982, 34, 141-145). These investigations showed that the presence of lubricants causes a decrease in cohesion of the tablets because they form a lubricated layer on the powder particles that are to be pressed together, thereby interfering with the bond between them.

This mechanism is also regarded as responsible for the decrease in strength of adhesion of the micronized drug particles on the carrier particles (Kassem, thesis, London University, 1990).

In WO 96/23485, the particles are mixed with a substance with anti-adherent or antifriction properties, consisting of one or more compounds selected from amino acids (in particular leucine), phospholipids or surfactants; deposition of the additive on the carrier is preferably carried out in the dry form, and does not give rise to a complete coating of the carrier, but rather to a discontinuous covering in order to saturate the highenergy sites. Preferably, the carrier particles and the additive are submitted to the corrasion process in a ball mill as described in WO 95/11666.

It follows from examination of the prior art that in the case of an inhalation powder, consisting of a drug-carrier mixture, efficient disaggregation of the active principle from the carrier during inhalation is dependent upon the drug-carrier interparticle forces and so depends on the surface characteristics of the latter.

The current market for Dry Powder Inhalers (DPIs) is expanding for several reasons including: environmental and technical concerns with pressurized metered dose inhalers, improved performance and acceptance of newly marketed DPIs, and the potential utility of DPIs for novel and systemically acting drug compounds. However, despite market growth, current DPIs have several shortcomings. Commercially available dry powder inhalers are generally less efficient and reproducible in delivering drugs to the lower airways than pressurized metered dose inhalers. Thus, several opportunities exist for improving the performance of DPIs including:

- increasing the fine particle fraction delivered (by inference, increasing lung deposition and reducing oropharyngeal deposition);
- decreasing variability of emitted dose and fine particle fraction;
- decreasing the dependence of dose delivered and region of delivery on inspiratory flow rate;
- decreasing inhaler resistance and energy required to disperse drug aerosol;
- increasing physical stability;
- improving ease of manufacture of DPIs;
- decreasing oropharyngeal deposition;
- enhancing control over regional lung deposition; and
- increasing pulmonary bioavailability.

There are other areas in which performance can be improved such as: increasing physical stability; and improving the ease of manufacture of DPIs and dry powder formulations. The most imminent needs of dry powder inhaler design are increasing the fine particle fraction and decreasing the variability between doses.

While DPI and MDI formulations of drug may be highly desirable, the number and type of suitable formulations that can be prepared is limited. This is due in large part to the limited compounds suitable as carriers in these dosage forms.

It is known in the art of inhalable powder formulations that the morphological and physicochemical properties of the drug and excipients (carrier) can affect the performance of a device used to administer the two. In particular, particle size of the drug and inert carrier has a great impact upon the ultimate site of delivery for each. A smaller particle size (less than about 10 microns) is accepted for lung delivery whereas larger particle sizes are preferred for tracheal, throat or buccal delivery with a DPI device. It is also known that the hygroscopicity of the drug and carrier can affect performance. Other factors known to affect the efficiency of delivery of a powdered solid with a DPI device include: electrostatic interactions between the drug and carrier particles, surface morphology of the particles, hydrophobicity/hydrophilicity of the drug and carrier particles, and others.

The desired properties of an inert carrier for use in a DPI include: 1) a particle diameter is within 50-1000 microns; 2) ability to associate with a drug sufficiently to aid in suspending it during a the period of administration balanced against an ability to dissociate from the drug in the buccal cavity or throat of a subject to permit pulmonary delivery of the drug but not of the carrier; 3) inertness toward degradation of the drug; 4) inertness in terms of not providing a therapeutic effect to a subject; 5) controllable and modifiable morphological properties; 6) suitability for preparation by a range of different processes; and/or 7) controllable and modifiable chemical properties.

Mono- or disaccharides, such as glucose, lactose, lactose monohydrate, sucrose or trehalose, sugar alcohols, such as mannitol or xylitol, polylactic acid, glucose, and trehalose are among the few compounds that are used as carriers in these devices. The properties of those compounds can be modified at least somewhat to optimize their performance. Even so, there are many drugs that cannot be suitably formulated with lactose for this type of administration. Therefore, identification of another material that is suitable as carrier and which properties can be modified in a controlled manner would be desired.

The current focus in DPI therapy is to administer higher concentrations of drug, use smaller unit dose volumes, develop new carriers having specific properties, identify and develop carriers suitable for use with specific DPI device formats.

In order to enhance drug absorption across the pulmonary lining, researchers have proposed the inclusion of permeation enhancers in DPI and PMDI devices. Cyclodextrins have been proposed for use in nebulizer liquid formulations as well as DPI and PMDI solid formulations. However, administration of some cyclodextrins into the lungs of a mammal might not be acceptable. Literature exists on the potential or observed toxicity of native cyclodextrins and cyclodextrin derivatives. The NTP Chemical Repository indicates that α-cyclodextrin may be harmful by inhalation. Nimbalkar et al. (*Biotechnol. Appl. Biochem.* (2001), 33, 123-125) cautions on the pulmonary use of an HP-β-CD/diacetyldapsone complex due to its initial effect of delaying cell growth of lung cells.

Even so, a number of studies regarding the use of cyclodextrins for inhalation have been reported although no ensuing formulations have been commercialized. The studies suggest that different drug-cyclodextrin combinations will be required for specific optimal or even useful inhaled or intra-nasal formulations. Attempts have been made to develop cyclodextrin-containing powders and solutions for buccal, pulmonary and/or nasal delivery.

A number of scientific publications and patent references disclose inhalable dry powder compositions comprising a cyclodextrin. For the most part, the cyclodextrin is included as an inclusion complex with the drug.

Rajewski et al. (*J. Pharm. Sci.* (1996), 85(11), 1142-1169) provide a review of the pharmaceutical applications of cyclodextrins. In that review, they cite studies evaluating the use of cyclodextrin complexes in dry powder inhalation systems.

U.S. Pregrant Patent Publication No. 2003-215512 and U.S. Pat. No. 6,309,671 to Billingsley et al. discloses a powdered inhalable composition wherein the drug is embedded within a glassy matrix formed of a cyclodextrin. As such, the drug is complexed with the drug and is not separable therefrom during administration with a DPI device.

Shao et al (*Eur. J. Pharm. Biopharm.* (1994), 40, 283-288) reported on the effectiveness of cyclodextrins as pulmonary absorption promoters. The relative effectiveness of cyclodextrins in enhancing pulmonary insulin absorption, as measured by pharmacodynamics, and relative efficiency was ranked as follows: dimethyl-β-cyclodextrin>α-cyclodextrin>β-cyclodextrin>γ-cyclodextrin>hydroxypropyl-β-cyclodextrin.

New Zealand Patent Application No. 510168 discloses a particulate composition for the delivery of a drug to the alveoli of the lung. The dry composition comprises the drug and at least 40% wt. of cyclodextrin. The particles are prepared by spray drying a liquid composition containing the cyclodextrin and drug, so the cyclodextrin is complexed with the drug and is not separable therefrom during administration of the composition with a DPI device.

Rodrigues et al. (Artificial Organs, (MAY 2003) Vol. 27, No. 5, pp. 492-497) disclose the preparation of particles containing a complex of insulin and cyclodextrin such that the two are delivered to the lung.

Nakate et al. (European Journal of Pharmaceutics and Biopharmaceutics (2003), 56(3), 319-325) disclose the administration of FK224 by DPI using β-CD particles in admixture with the drug. The formulation is made by simultaneous micronization of the FK224 and β-CD such that both are of a particle size suitable for delivery to the lungs.

Fukaya et al. (European Respiratory Journal (2003), 22(2), 213-219) disclose the results of an evaluation of a DPI dry powder formulation containing a complex of cyclosporin A and a cyclodextrin.

Kinnarinen et al. (Journal of Controlled Release (2003), 90(2), 197-205) disclose a DPI formulation comprising a complex of budesonide and γ-CD.

Vozone et al. (Journal of Inclusion Phenomena and Macrocyclic Chemistry (2002), Volume Date 2003, 44(1-4), 111-115) disclose the administration of budesonide and dimethyl-β-CD present as either a preformed complex or physical mixture in a composition for dry powder inhalation. They observed no statistically significant difference between the emitted dose means of both the complex and the physical mixture, but they observed a statistically significant higher fine particle fraction mean was for the complex. They suggest that using a spray-dried CD complex powder for pulmonary drug delivery may increase the drug's respirable fraction and consequently its therapeutic efficacy.

PCT International Publication No. WO 01/87278 to Kampinga discloses the preparation and use of particles containing 10-40% of drug and 90-60% of a saccharide, which can be cyclodextrin. If a cyclodextrin were present, it would be complexed with the drug due to the method of preparation employed.

Camoes et al. (Proceedings of the International Symposium on Controlled Release of Bioactive Materials (2000), 27th, 794-795) disclose β-CD complexes with salbutamol for dry powder inhalation.

Pinto et al. (S.T.P. Pharma Sciences (1999), 9(3), 253-256) disclose HP-β-CD complexes with beclomethasone and use thereof in a dry powder inhalable formulation.

U.S. Pat. No. 6,582,728 to Platz et al. discloses a dry powder inhalable formulation comprising a drug and a carrier, which can be cyclodextrin. The formulation is prepared by spray drying the drug and carrier together. If a cyclodextrin were the carrier, it would be complexed with the drug due to the method of preparation.

European Patent No. 1283035 discloses an inhalable dry powder formulation comprising parathyroid hormone, an absorption enhancer and a coarse particle carrier. The cyclodextrin can be an enhancer, but it is not suggested as being a suitable carrier. Since it is an absorption enhancer, it is delivered into the lungs with the drug.

U.S. Pregrant Patent Publication No. 2003-0138403 to Drustrup discloses formulations containing interferon and SAE-CD. The formulations are suggested as being suitable for administration by inhalation. The formulations contain the preformed complex of interferon and SAE-CD.

U.S. Pregrant Patent Publications No. 2003-064928 to Backstrom et al. and No. 2003-059376 to Libbey et al. and U.S. Pat. Nos. 6,436,902 and 5,952,008 to Backstrom et al. disclose inhalable formulations wherein cyclodextrin is incorporated into the matrix of particles to enhance the absorption of drug in the lung. The cyclodextrin is not separable from the drug during administration.

U.S. Pat. No. 6,599,535 to Guitard et al. discloses solid dispersion compositions comprising a macrolide drug and a carrier medium, which can be a cyclodextrin. A number of water soluble cyclodextrin derivatives are suggested, including SAE-CD; however, the process for preparing the composition results in complexation of the drug and cyclodextrin. So, the drug and cyclodextrin are both delivered to the lung.

U.S. Pregrant Patent Publications No. 2002-117170 to Platz et al. discloses a spray-dried composition containing FSH and a pharmaceutically acceptable carrier, which can be a cyclodextrin. It is likely that the FSA and cyclodextrin would be present as a complex due to the spray-drying process described in the application.

U.S. Pat. No. 6,495,120 to McCoy et al. discloses the pulmonary administration of a drug, HP-β-CD and a carrier solvent. The formulation comprises the drug, a cyclodextrin and a solvent, so the drug is complexed with the cyclodextrin.

U.S. Pat. No. 6,306,440 to Backstrom et al. discloses inhalable formulations comprising insulin and an absorption enhancer, such as a cyclodextrin. Both the cyclodextrin and insulin are intended to be delivered to the lung.

van der Kuy et al. (Eur. J. Clin. Pharmacol. (1999 November), 55(9), 677-80) report the results of the pharmacokinetic properties of two intranasal preparations of dihydroergotamine mesylate (DHEM)-containing formulation using a commercially available intranasal preparation. The formulations also contained randomly methylated β-cyclodextrin (RAMEB). No statistically significant differences were found in maximum plasma concentration (Cmax), time to reach Cmax (tmax), area under plasma concentration-time curve (AUC0-8 h), Frel(t=8 h) and Cmax/AUC(t=8 h) for the three intranasal preparations. The results indicate that the pharmacokinetic properties of the intranasal preparations are not significantly different from the commercially available nasal spray.

U.S. Pat. Nos. 5,942,251 and 5,756,483 to Merkus cover pharmaceutical compositions for the intranasal administration of dihydroergotamine, apomorphine and morphine comprising one of these pharmacologically active ingredients in combination with a cyclodextrin and/or a disaccharide and/or a polysaccharide and/or a sugar alcohol.

U.S. Pat. No. 5,955,454 discloses a pharmaceutical preparation suitable for nasal administration containing a progestogen and a methylated β-cyclodextrin having a degree of substitution of between 0.5 and 3.0.

U.S. Pat. No. 5,977,070 to Piazza et al. discloses a pharmaceutical composition for the nasal delivery of compounds useful for treating osteoporosis, comprising an effective amount of a physiologically active truncated analog of PTH or PTHrp, or salt thereof and an absorption enhancer selected from the group consisting of dimethyl-β-cyclodextrin.

PCT International Publication No. WO 00/015,262 to Clark et al. discloses inhalable powdered compositions comprising a hygroscopic growth inhibitor and a drug. The inhibitor can be a cyclodextrin among other things, and SBE-CD is exemplified as a suitable cyclodextrin. The cyclodextrin is complexed with the drug in the formulation due to the process of preparation employed.

PCT International Publication No. WO 00/066,206 to Thurston et al. discloses a multi-component inhalable composition, wherein a cyclodextrin can be included as a drug stabilizing agent. The cyclodextrin is complexed with the drug in the formulation due to the process of preparation employed.

Other references suggest the use, in general, of a cyclodextrin as a carrier in a DPI formulation. PCT International Publication No. WO 01/05429 to Caponetti et al. discloses the use of mixtures suitable for dry powder inhalation. The compositions comprise smooth carrier particles in admixture with a drug. Cyclodextrins, among other things, are suggested as being suitable for the carrier. There is no exemplification of such a use. The carrier particles are made by smoothing the surface of rough particles in a high speed mixer granulator alternately in the presence of a solvent or in dry form.

U.S. Pat. No. 6,645,466 to Keller et al. discloses a dry powder formulation for inhalation. The formulation contains a fine inhalable particle size drug, a coarser non-inhalable particle size carrier and magnesium stearate bound to the carrier. A cyclodextrin can apparently serve as the carrier. There is no disclosure regarding examples or preferred properties for the cyclodextrin as carrier, nor is there any disclosure of a method of preparing the CD to make it suitable as the carrier.

The parent cyclodextrins contain 6, 7, or 8 glucopyranose units and are referred to as α-, β-, and γ-cyclodextrin respectively. Each cyclodextrin subunit has secondary hydroxyl groups at the 2 and 3 positions and a primary hydroxyl group at the 6-position. The cyclodextrins may be pictured as hollow truncated cones with hydrophilic exterior surfaces and hydrophobic interior cavities.

The physical and chemical properties of the parent cyclodextrins can be modified by

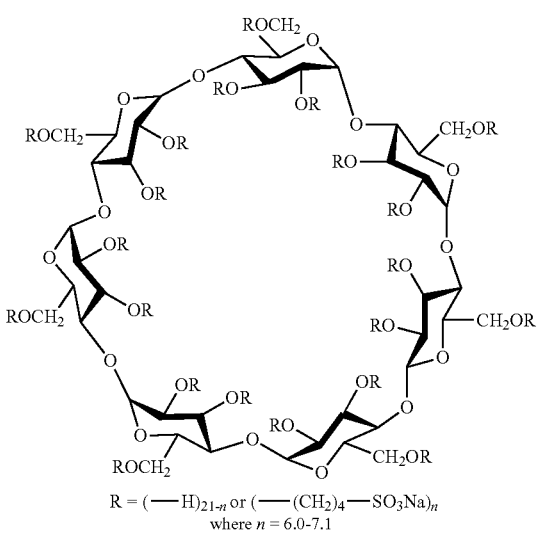

Sulfobutyl Ether-β-Cylodextrin (Captisol®)

derivatizing the hydroxyl groups with other functional groups. One such derivative is a sulfoalkyl ether cyclodextrin. A sulfobutyl ether derivative of beta cyclodextrin (SBE-β-CD), in particular the derivative with an average of about 7 substituents per cyclodextrin molecule (SBE7-β-CD), has been commercialized by CyDex, Inc. as CAPTISOL®. The anionic sulfobutyl ether substituent dramatically improves the aqueous solubility of the parent cyclodextrin. In addition, the presence of the charges decreases the ability of the molecule to complex with cholesterol as compared to the hydroxypropyl derivative. Reversible, non-covalent, complexation of drugs with CAPTISOL® cyclodextrin generally allows for increased solubility and stability of drugs in aqueous solutions. While CAPTISOL® is a relatively new but known cyclodextrin, some references specifically directed to SAE-CD's disclose its use in an inhalable liquid formulation. Even so, its use in the preparation of solid dry powder formulations for a DPI has not previously been evaluated.

U.S. Pat. No. 5,874,418 to Stella et al. discloses solid formulations comprising a physical mixture of a drug and an SAE-CD, wherein a major portion of the drug is not complexed with the SAE-CD. However, Stella et al. do not suggest that such a formulation is suitable for administration via inhalation, in particular with a DPI or PMDI device. They also do not disclose any methods of controlling or varying the morphological and physicochemical properties of the SAE-CD, so one of the art would not be able to prepare forms of SAE-CD that are suitable for DPI administration.

Another such derivative is hydroxypropyl-β-cyclodextrin (HP-β-CD). Müller et al. (*Proceed. Int'l. Symp. Control. Rel. Bioact. Mater.* (1997), 24, 69-70) discloses the results of a study on the preparation of budesonide microparticles by an ASES supercritical carbon dioxide process for use in a dry powder inhaler. HP-β-CD is suggested as a carrier for a powder.

Pinto et al. (S.T.P. *Pharma. Sciences* (1999), 9(3), 253-256) disclose the results of a study on the use of HP-β-CD in an inhalable dry powder formulation for beclomethasone. The HP-β-CD was evaluated as a complex or physical mixture with the drug in a study of in vitro deposition of the emitted dose from a MICRO-HALER™ inhalation device. The amount of respirable drug fraction was reportedly highest with the complex and lowest with the micronized drug alone.

Williams et al. (*Eur. J. Pharm. Biopharm.* (1999 March), 47(2), 145-52) reported the results of a study to determine the influence of the formulation technique for 2-hydroxypropyl-beta-cyclodextrin (HP-β-CD) on the stability of aspirin in a suspension-based pressurized metered-dose inhaler (pMDI) formulation containing a hydrofluoroalkane (HFA) propellant. HP-β-CD was formulated in a pMDI as a lyophilized inclusion complex or a physical mixture with aspirin. Aspirin in the lyophilized inclusion complex exhibited the most significant degree of degradation during the 6-months storage, while aspirin alone in the pMDI demonstrated a moderate degree of degradation. Aspirin formulated in the physical mixture displayed the least degree of degradation. Reportedly, HP-β-CD may be used to enhance the stability of a chemically labile drug, but the drug stability may be affected by the method of preparation of the formulation.

Worth et al. (24th *International Symposium on Controlled Release of Bioactive Materials* (1997)) disclose the results of a study evaluating the utility of steroid/cyclodextrin complexes for pulmonary delivery. In side-by-side comparisons, β-CD, SBE7-β-CD, and HP-β-CD were evaluated according to their ability to form inclusion complexes with beclomethasone dipropionate (BDP) and its active metabolite beclomethasone monopropionate (BMP). BMP was more easily solubilized with a cyclodextrin, and the observed order of solubilizing power was: HP-β-CD (highest)>β-CD>SBE7-β-CD. Although no results regarding actual utility in an inhaled formulation were disclosed, they suggest that BMP rather than BDP would be a better alternative for development of a nebulizer solution.

Kinnarinen et al. (11th *International Cyclodextrin Symposium* CD, (2002)) disclose the results of a study of the in vitro pulmonary deposition of a budesonide/γ-CD inclusion complex for dry powder inhalation. No advantage was observed by complexation with γ-CD. Vozone et al. (11th *International Cyclodextrin Symposium* CD, (2002)) disclose the results of a study on the complexation of budesonide with γ-cyclodextrin for use in dry powder inhalation. No difference was observed within emitted doses of the cyclodextrin complex or a physical mixture of budesonide and the CD. But, a difference observed in the fine particle fraction of both formulations suggested that use of a cyclodextrin complex for pulmonary drug delivery might increase the respirable fraction.

Gudmundsdottir et al. (*Pharmazie* (2001 December), 56(12), 963-6) disclose the results of a study in which midazolam was formulated in aqueous sulfobutylether-beta-cyclodextrin buffer solution. The nasal spray was tested in healthy volunteers and compared to intravenous midazolam in an open crossover trial. The nasal formulation reportedly approaches the intravenous form in speed of absorption, serum concentration and clinical sedation effect. No serious side effects were observed.

Srichana et al. (*Respir. Med.* (2001 June), 95(6), 513-9) report the results of a study to develop a new carrier in dry powder aerosols. Two types of cyclodextrin were chosen; gamma cyclodextrin (γ-CD) and dimethyl-beta-cyclodextrin (DMCD) as carriers in dry powder formulations. Salbutamol was used as a model drug and a control formulation containing lactose and the drug was included. A twin-stage impinger (TSI) was used to evaluate in delivery efficiency of those dry powder formulations. From the results obtained, it was found that the formulation containing γ-CD enhanced drug delivery to the lower stage of the TSI (deposition=65%) much greater than that of both formulations containing DMCD (50%) and the control formulation (40%) (P<0.05). The haemolysis of red blood cells incubated with the DMCD complex was higher than that obtained in the γ-CD complex. The drug release in both formulations containing γ-CD and DMCD was fast (over 70% was released in 5 min) and nearly all the drug was released within 30 min.

U.S. Pat. No. 6,436,902 to Backstrom et al. discloses compositions and methods for the pulmonary administration of a parathyroid hormone in the form of a dry powder suitable for inhalation in which at least 50% of the dry powder consists of (a) particles having a diameter of up to 10 microns; or (b) agglomerates of such particles. A dry powder inhaler device contains a preparation consisting of a dry powder comprising (i) a parathyroid hormone (PTH), and (ii) a substance that enhances the absorption of PTH in the lower respiratory tract, wherein at least 50% of (i) and (ii) consists of primary particles having a diameter of up to 10 microns, and wherein the substance is selected from the group consisting of a salt of a fatty acid, a bile salt or derivative thereof, a phospholipid, and a cyclodextrin or derivative thereof.

U.S. Pat. No. 6,518,239 to Kuo et al. discloses a dispersible aerosol formulation comprising an active agent and a dipeptide or tripeptide for aerosolized administration to the lung. The compositions reportedly may also include polymeric excipients/additives, e.g., polyvinylpyrrolidones, derivatized celluloses such as hydroxymethylcellulose, hydroxyethylcellulose, and hydroxypropyl methylcellulose, Ficolls (a polymeric sugar), hydroxyethylstarch, dextrates (e.g., cyclodextrins, such as 2-hydroxypropyl-β-cyclodextrin and sulfobutylether-β-cyclodextrin), polyethylene glycols, and pectin.

PCT International Publication No. WO 03/066,031 to Mueller et al. of PharmaTech Gmbh discloses a suspension formulation for use in a pMDI. The suspension comprises a drug, propellant and a cyclodextrin derivative, which can be a hydroxyalkyl ether cyclodextrin or a sulfoalkyl ether cyclodextrin, among other CD derivatives.

Nakate et al. (*Eur. J. Pharm. Biopharm.* (2003 March), 55(2), 147-54) disclose the results of a study to determine the improvement of pulmonary absorption of the cyclopeptide FK224 (low aqueous solubility) in rats by co-formulating it with beta-cyclodextrin. The purpose of the study was to investigate the effect of pulmonary delivery on the systemic absorption of FK224 in comparison with other administration routes, and to determine the bioavailability (BA) of FK224 following pulmonary administration in rats using various dosage forms. After administration of an aqueous suspension, the bioavailability was reduced to 2.7% compared with 16.8% for the solution. However, β-cyclodextrin (β-CD) was found to be an effective additive as far as improving the solubility of FK224 was concerned. The bioavailability of the aqueous suspension containing β-CD was increased to 19.2%. It was observed that both the C(max) and AUC of FK224 were increased as the amount of n-CD increased. The plasma profiles showed sustained absorption. They suggest that β-CD or derivatives with various degrees of aqueous solubility are potential drug carriers for controlling pulmonary absorption.

Kobayashi et al. (*Pharm. Res.* (1996 Jan), 13(1), 80-3) disclose the results of a study on pulmonary delivery of salmon calcitonin (sCT) dry powders containing absorption enhancers in rats. After intratracheal administration of sCT dry powder and liquid (solution) preparations to rats, plasma sCT levels and calcium levels were measured. Reportedly, sCT in the dry powder and in the liquid were absorbed nearly to the same degree. Absorption enhancers (oleic acid, lecithin, citric acid, taurocholic acid, dimethyl-β-cyclodextrin, octyl-β-D-glucoside) were much more effective in the dry powder than in the solution.

Adjei et al. (*Pharm. Res.* (1992 February), 9(2), 244-9) disclose the results of a study on the bioavailability of leuprolide acetate following nasal and inhalation delivery to rats and healthy humans. Systemic delivery of leuprolide acetate, a luteinizing hormone releasing hormone (LHRH) agonist, was compared after inhalation (i.h.) and intranasal (i.n.) administration. The i.n. bioavailability in rats was significantly increased by α-cyclodextrin (CD), EDTA, and solution volume. Absorption ranged from 8 to 46% compared to i.v. controls. Studies in healthy human males were conducted with leuprolide acetate i.n. by spray, or inhalation aerosol (i.h.), and subcutaneous (s.c.) and intravenous (i.v.) injection. The s.c. injection was 94% bioavailable compared with i.v. The i.n. bioavailability averaged 2.4%, with significant subject-to-subject variability. Inhalation delivery gave a slightly lower intersubject variability. Mean Cmax with a 1-mg dose of solution aerosol was 0.97 ng/ml, compared with 4.4 and 11.4 ng/ml for suspension aerosols given at 1- and 2-mg bolus dosages, respectively. The mean bioavailability of the suspension aerosols (28% relative to s.c. administration) was fourfold greater than that of the solution aerosol (6.6%).

CyDex (*Cyclopedia* (2002), 5(1), 3) discloses that SBE-CD is non-toxic to rats in an inhaled aerosol composition when present alone.

The most imminent needs in dry powder inhaler design are: increasing the fine particle fraction (mass), and decreasing the variability between doses. Lactose is the only carrier particle used in FDA-approved DPIs the US, and it is known to exhibit large batch-to-batch variability in performance. Thus, further opportunities to improve material properties and process variables exist.

In summary, the art discloses inhalable dry powder formulations containing an inhalable drug and cyclodextrin; however, in almost every case, the cyclodextrin is present as an inclusion complex with the drug. In the few instances that the cyclodextrin has been suggested as a carrier, it is generally used as an absorption enhancer. To the knowledge of the present inventors, the art does not suggest that a water soluble cyclodextrin derivative, in particular a sulfoalkyl ether cyclodextrin (SAE-CD) would be suitable as a carrier in a DPI device, such that the drug and not the SAE-CD is delivered to the lungs after administration. Neither does the art provide any material which morphological, chemical and physicochemical properties are easily modified and adapted for suitable use in a DPI device with a wide range of different drugs. They also fail to provide a carrier suitable for use in DPI devices of different formats, particularly those that have low or high pressure drops.

A need remains in the art for a carrier material that provides significant advantages over lactose and other carriers, that is suitable for administration in dry powder form with a DPI, and that has readily modifiable morphological and physicochemical and chemical properties that can be adapted to optimize interaction with an active agent in a dry powder formulation for DPI.

SUMMARY OF THE INVENTION

The present invention seeks to overcome the disadvantages present in known dry powder formulations. As such, a derivatized cyclodextrin-based, e.g., sulfoalkyl ether cyclodextrin (SAE-CD)-based, inhalable dry powder formulation is provided. The present formulation includes a principle active agent and SAE-CD as a carrier.

The properties of SAE-CD carrier particles can be modulated such that different physicochemical properties are matched to drug particle properties for optimizing dispersion from dry powder inhalers.

Depending upon the drug properties, particle size, size distribution, morphological properties, and electrostatic charge, the characteristics of the SAE-CD can be modulated through a variety of techniques to yield drug-carrier interactions that promote greater dispersion and flow independent drug delivery from passive dry powder inhaled delivery systems. The properties can be adapted for particular uses by changing the identity of the counterion, changing the alkyl chain length, average degree of substitution, or ring size of the parent cyclodextrin from which the SAE-CD is made.

Moreover, the present formulation possesses other advantages over materials such as lactose. Unlike lactose, which is optimal for use in only a few different DPI device formats, SAE-CD as a solid carrier is suitable for use in DPI devices having a low, moderate and high pressure drop.

When compared to lactose, SAE-CD as a carrier exhibits the following advantages as determined by evaluations in DPI devices:

The variability of emitted dose and the fine particle fraction is less for the SAE-CD powder, especially for SAE-CD powder derived from attritted foam, than for the lactose standard.

The dispersion of drug from SAE-CD powder, especially that derived from attritted foam, is independent of pressure drop (inspiratory flow rate); whereas, the lactose powder showed pressure drop dependency.

Inhaler resistance and energy required to disperse drug aerosol can be reduced for the SAE-CD, especially for SAE-CD powder derived from attritted foam, compared to the lactose without influencing aerosol delivery. This will allow for efficient operation of a dry powder inhaler by patients with increased airway obstruction (e.g. asthma) and those with age-related reduction in peak inhalation rates (young and elderly).

The fine particle fraction delivered by SAE-CD, especially for SAE-CD powder derived from attritted foam, is comparable to the lactose standard.

SAE-CD is included in a dry powder formulation in admixture with a therapeutic agent such that all or substantially all of the drug is not complexed with the SAE-CD. During use, the SAE-CD serves as a carrier that facilitates transfer of the drug from the container of the DPI past the buccal cavity, throat oropharyngeal cavity and into the lung. However, the SAE-CD particles possess morphological and physicochemical properties that predispose them to separate from the drug particles, such that the drug particles are delivered to the lung but the SAE-CD particles are not. In other words, the SAE-CD particles and drug particles are attracted to each other enough to permit simultaneous delivery thereof into the buccal cavity, throat or oropharyngeal cavity, however, the SAE-CD and drug particles become dissociated from one another such that the drug particles continue on to the lungs but the SAE-CD particles do not, i.e., they are deposited in the buccal cavity or throat. The SAE-CD particles are preferably prepared by a particular method in order to provide particular morphological and physicochemical properties.

When SAE-CD particles are prepared by some methods, unsuitable particles are formed; therefore, SAE-CD particles disclosed herein are prepared by a method that provides plural particles suitable for administration by DPI as disclosed herein. In one embodiment, the process for preparing an SAE-CD dry powder carrier comprises the steps of:

providing an aqueous solution comprising water, SAE-CD and optionally one or more other materials;

converting the solution to a foam;

optionally, freezing the foam;

dehydrating the foam to form a friable porous glass, which may or may not be particulate;

attritting the porous glass to form microparticles; and screening the microparticles, thereby forming a dry powder carrier.

Specific embodiments of the method of the invention include those wherein: 1) the dry powder carrier is screened until substantially all of the carrier passes through a 40-mesh sieve; 2) the solution is converted to a foam by bubbling an inert gas, such as nitrogen, through the solution; 3) the foam is dehydrated by freeze drying or lyophilization; 4) the microparticles have a median particle size distribution less than 420 microns in diameter; 5) the foam is attritted in a low energy attritor.

Another aspect of the invention provides an inhalable therapeutic dry powder suitable for administration to a subject with a DPI device, the powder comprising:

a first particulate composition comprising an active agent suitable for administration via inhalation, wherein the particulate composition has a particle size distribution such that substantially all (at least 90% or 95%) of the particles are less than 37 microns in diameter (400-mesh) sieve; and a second particulate composition comprising SAE-CD, wherein the particulate composition has a particle size distribution such that substantially all of the particles therein pass through a 420 micron (40-mesh) sieve.

Specific embodiments of the invention include those wherein: 1) the SAE-CD is made according to a process of the invention as described herein; 2) the second particulate composition has a substantially smooth surface; 3) first particulate composition has a median diameter of less than 10 microns; 4) the dry powder formulation has a moisture content of less than about 10% wt.; 5) the first particulate composition has an electrostatic charge more negative than about −2 nC/g, and the second particulate composition has an electrostatic charge in the range of about 0-1.5; 6) the first particulate composition has an electrostatic charge of about −2 to −0.5 nC/g, and the second particulate composition has an electrostatic charge in the range of about −0.5 to −2; 7) the first particulate composition has an electrostatic charge of about 0.5 to −0.5 nC/g, and the second particulate composition has an electrostatic charge in the range of about −2 to 2; 8) the second particulate composition has been prepared by attritting a dehydrated foam comprising SAE-CD; 9) the second particulate composition is an agglomerate of smaller particles; 10) the surface of the particles in the second particulate composition is substantially smooth as determined by microscopy; 11) the SAE-CD is present in amorphous form; 12) an excipient in the carrier is present in crystalline form; 13) the active agent is present in crystalline form; 14) the active agent is present in amorphous form; 15) the second particulate composition has a particle size distribution such that at least 50% of the particles therein are less than about 80 microns in diameter; 16) the second particulate composition has a median particle diameter in the range of about 10 to 300 microns, 25 to 300 microns, 37 to 125 microns; 17) the second particulate composition has a moisture content of less than about 10% wt, 8% wt., 7% wt., 2.5% wt. or 1% wt., or a moisture content in the range of about 0.01% to about 10% wt., or about 0.1% to about 5% wt.

In one aspect, an SAE-CD-based dry powder composition is prepared by a particular process and possesses specified morphological and physicochemical properties as described herein. In another aspect, an inhalable dry powder formulation comprising a drug and the SAE-CD of specified morphological and physicochemical properties is prepared as described herein. Another aspect provides for the use of the so-characterized SAE-CD dry powder as a carrier for delivery of a drug via a DPI. The invention also provides a method of treating diseases or disorders by administration of the so-characterized SAE-CD-based dry powder formulation with a DPI device.

Specific embodiments of the invention include those wherein: 1) the SAE-CD is a compound of the formula 1 or a mixture thereof; 2) the dry powder composition further comprises an antioxidant, acidifying agent, alkalizing agent, buffering agent, solubility-enhancing agent, penetration enhancer, electrolyte, fragrance, glucose, glidant, stabilizer, bulking agent, cryoprotectant, plasticizer, flavors, sweeteners, surface tension modifier, density modifier, volatility modifier, or a combination thereof; 3) the SAE-CD is a compound of the formula 2 or a mixture thereof.

These and other aspects of this invention will be apparent upon reference to the following detailed description, examples, claims and attached figures.

BRIEF DESCRIPTION OF THE FIGURES

The following drawings are given by way of illustration only, and thus are not intended to limit the scope of the present invention.

DETAILED DESCRIPTION OF THE INVENTION

Figure 1:
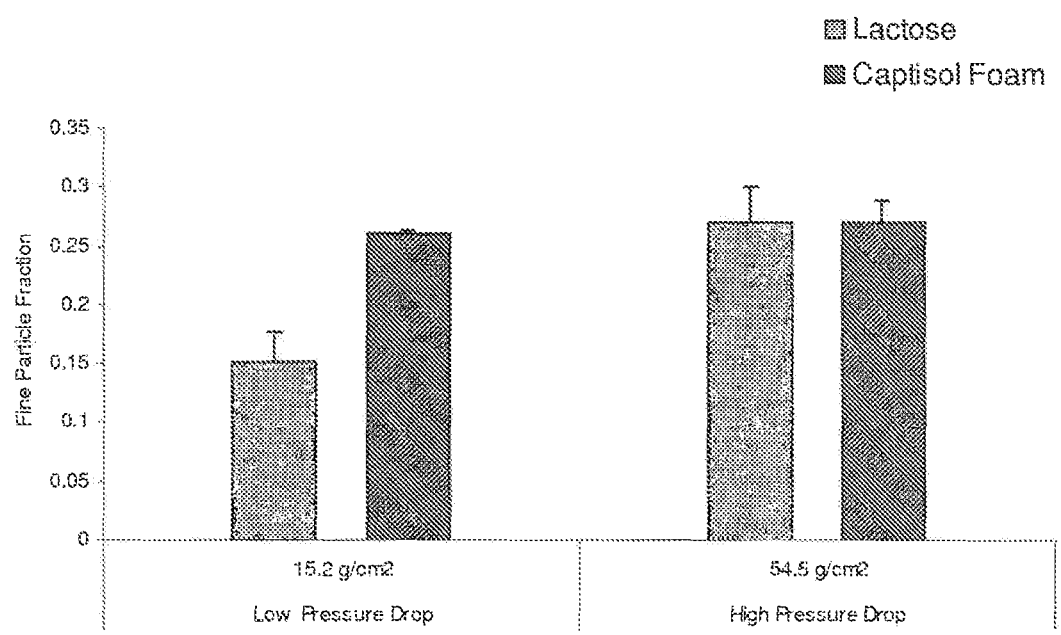
FIG. 1 depicts a chart of the fine particle fraction of cromolyn (formulated with lactose and Captisol® attritted foam) as a function of pressure drop differences in the devices used (Mean+SD for CAPTISOL® as compared to the same for lactose).

The presently claimed formulation overcomes many of the undesired properties of other known inhalable dry powder formulations. By including SAE-CD in an inhalable dry powder formulation, one is able to adapt the physicochemical, chemical and morphological properties of the powder.

As used herein, the term attritting means to physically abrade a solid to reduce its particle size. Any such process used in the pharmaceutical industry is suitable for use in the process of the invention. Attrition processes include, by way of example and without limitation, micronizing, ball milling, jet milling, hammer mining, pin milling, tumbling, sieving, mortar and pestle. Both low and high energy methods can be used.

The dry powder inhalable DPI formulation includes a therapeutic agent that is suitable for administration via inhalation. The drug is present in an amount sufficient for single dose or multi-dose administration, meaning that the formulation can be packaged in single or multiple use forms.

The dry powder of the invention can be use in any known DPI device. Exemplary ones include those listed herein and many others described in the scientific and patent literature.

The present invention provides SAE-CD based formulations, wherein the SAE-CD is a compound of the Formula 1:

Formula 1 wherein:

n is 4, 5 or 6;

$R_1$, $R_2$, $R_3$, $R_4$, $R_5$, $R_6$, $R_7$, $R_8$ and $R_9$ are each, independently, $O^-$ or a $O$—($C_{2-6}$ alkylene)-$SO_3^-$ group, wherein at least one of $R_1$ to $R_9$ is independently a $O$—($C_2$-$C_6$ alkylene)-$SO_3^-$ group, preferably a $O$—$(CH_2)_m SO_3^-$ group, wherein m is 2 to 6, preferably 2 to 4 (e.g., $OCH_2CH_2CH_2SO_3^-$ or $OCH_2CH_2CH_2CH_2SO_3^-$); and $S_1$, $S_2$, $S_3$, $S_4$, $S_5$, $S_6$, $S_7$, $S_8$ and $S_9$ are each, independently, a pharmaceutically acceptable cation which includes, for example, $H^+$, alkali metals (e.g., $Li^+$, $Na^+$, $K^+$), alkaline earth metals (e.g., $Ca^{+2}$, $Mg^{+2}$), ammonium ions and amine cations such as the cations of $C_1$-$C_6$alkylamines, piperidine, pyrazine, $C_1$-$C_6$ alkanolamine and $C_4$-$C_8$ cycloalkanolamine.

The SAE-CD used is described in U.S. Pat. No. 5,376,645 and No. 5,134,127 to Stella et al, the entire disclosures of which are hereby incorporated by reference. U.S. Pat. No. 3,426,011 to Parmerter et al. discloses anionic cyclodextrin derivatives having sulfoalkyl ether substituents. Lammers et al. (*Recl. Trav. Chim. Pays-Bas* (1972), 91(6), 733-742); *Staerke* (1971), 23(5), 167-171) and Qu et al. (*J. Inclusion Phenom. Macro. Chem.*, (2002), 43, 213-221) disclose sulfoalkyl ether derivatized cyclodextrins. An SAE-CD can be made according to the disclosures of Stella et al., Parmerter et al., Lammers et al. or Qu et al., and optionally purified to remove the major portion of the underivatized parent cyclodextrin, used according to the present invention.

The terms "alkylene" and "alkyl," as used herein (e.g., in the $O$—($C_2$-$C_6$ alkylene)-$SO_3^-$ group or in the alkylamines), include linear, cyclic, and branched, saturated and unsaturated (i.e., containing one double bond) divalent alkylene groups and monovalent alkyl groups, respectively. The term "alkanol" in this text likewise includes both linear, cyclic and branched, saturated and unsaturated alkyl components of the alkanol groups, in which the hydroxyl groups may be situated at any position on the alkyl moiety. The term "cycloalkanol" includes unsubstituted or substituted (e.g., by methyl or ethyl) cyclic alcohols.

An embodiment of the present invention provides compositions containing a single type of or a mixture of cyclodextrin derivatives, having the structure set out in formula (I), where the composition overall contains on the average at least 1 and up to 3 n+6 alkylsulfonic acid moieties per cyclodextrin molecule. The present invention also provides compositions containing a single type of cyclodextrin derivative, or at least 50% of a single type of cyclodextrin derivative. The invention also includes formulations containing cyclodextrin derivatives having a narrow or wide and high or low degree of substitution. These combinations can be optimized as needed to provide cyclodextrins having particular properties.

Exemplary SAE-CD derivatives include SBE4-β-CD, SBE7-β-CD, SBE11-β-CD, and SBE5-γ-CD which correspond to SAE-CD derivatives of the formula I wherein n=5, 5, 5 and 6, resepectively; m is 4; and there are on average 4, 7, 11 and 5 sulfoalkyl ether substituents present, respectively. Other exemplary SAE-CD derivatives include those of the formula SAEx-R-CD (Formula 2), wherein SAE is sulfomethyl ether (SME), sulfoethyl ether (SEE), sulfopropyl ether (SPE), sulfobutyl ether (SBE), sulfopentyl ether (SPtE), or sulfohexyl ether (SHE); x (average or specific degree of substitution) is 1-18, 1-21, 1-24, when R (ring structure of parent cyclodextrin) is α, β or γ, respectively; and CD is cyclodextrin.

Since SAE-CD is a poly-anionic cyclodextrin, it can be provided in different salt forms. Suitable counterions include cationic organic atoms or molecules and cationic inorganic atoms or molecules. The SAE-CD can include a single type of counterion or a mixture of different counterions. The properties of the SAE-CD can be modified by changing the identity of the counterion present. For example, a first salt form of SAE-CD can have a greater electrostatic charge than a different second salt form of SAE-CD. The calcium salt form has been found to be more electronegative than the sodium salt form. Likewise, an SAE-CD having a first degree of substitution can have a greater electrostatic charge than a second SAE-CD having a different degree of substitution.

By "complexed" is meant "being part of a clathrate or inclusion complex with", i.e., a complexed therapeutic agent is part of a clathrate or inclusion complex with a cyclodextrin derivative. By "major portion" is meant at least about 50% by weight. Thus, a formulation according to the present invention contains an active agent of which more than about 50% by weight is not complexed with a cyclodextrin. The actual percent of active agent that is complexed will vary according to the specific cyclodextrin and specific active agent employed. The invention also includes embodiments wherein a minor portion of the active agent is complexed with the derivatized cyclodextrin. It also includes embodiments wherein in substantially all (at least 90% wt., at least 95% wt. or at least 98% wt.) of the active agent is not complexed with an SAE-CD. Embodiments wherein none of the active agent is complexed with SAE-CD are also included.

The present invention also provides compositions containing a mixture of cyclodextrin derivatives wherein two or more different types of cyclodextrin derivatives are included in the composition. By different types, is meant cyclodextrins derivatized with different types of functional groups e.g., hydroxyalkyl and sulfoalkyl, and not to the heterogeneous nature of derivatized cyclodextrins due to their varying degrees of substitution. Each independent different type can contain one or more functional groups, e.g. SBE-CD where the cyclodextrin ring has only sulfobutyl functional groups, and hydroxypropyl-ethyl-β-CD where the cyclodextrin ring has both hydroxypropyl functional groups and ethyl functional groups. The amount of each type of cyclodextrin derivative present can be varied as desired to provide a mixture having the desired properties.

Other cyclodextrin derivatives that can be used in combination with SAE-CD according to the invention include the hydroxyethyl, hydroxypropyl (including 2- and 3-hydroxypropyl) and dihydroxypropyl ethers, their corresponding mixed ethers and further mixed ethers with methyl or ethyl groups, such as methylhydroxyethyl, ethyl-hydroxyethyl and ethyl-hydroxypropyl ethers of alpha-, beta- and gamma-cyclodextrin; and the maltosyl, glucosyl and maltotriosyl derivatives of alpha, beta- and gamma-cyclodextrin, which may contain one or more sugar residues, e.g. glucosyl or diglucosyl, maltosyl or dimaltosyl, as well as various mixtures thereof, e.g. a mixture of maltosyl and dimaltosyl derivatives. Specific cyclodextrin derivatives for use herein include hydroxypropyl-beta-cyclodextrin, hydroxyethyl-beta-cyclodextrin, hydroxypropyl-gamma-cyclodextrin, hydroxyethyl-γ-cyclodextrin, dihydroxypropyl-beta-cyclodextrin, glucosyl-alpha-cyclodextrin, glucosyl-beta-cyclodextrin, diglucosyl-beta-cyclodextrin, maltosyl-alpha-cyclodextrin, maltosyl-beta-cyclodextrin, maltosyl-gamma-cyclodextrin, maltotriosyl-beta-cyclodextrin, maltotriosyl-gamma-cyclodextrin and dimaltosyl-beta-cyclodextrin, and mixtures thereof such as maltosyl-beta-cyclodextrin/dimaltosyl-beta-cyclodextrin, as well as methyl-beta-cyclodextrin. Procedures for preparing such cyclodextrin derivatives are well-known, for example, from Bodor U.S. Pat. No. 5,024,998 dated Jun. 18, 1991, and references cited therein.

The carrier of the invention can also include a combination of derivatized cyclodextrin (SAE-CD) and underivatized cyclodextrin.

The HP-β-CD can be obtained from Research Diagnostics Inc. (Flanders, N.J.). HP-β-CD is available with different degrees of substitution. Exemplary products include ENCAPSIN™ (degree of substitution-4; HP4-β-CD) and MOLECUSOL™ (degree of substitution-8; HP8-β-CD); however, embodiments including other degrees of substitution are also available. Since HPCD is non-ionic, it is not available in salt form.

Dimethyl cyclodextrin is available from FLUKA Chemie (Buchs, CH) or Wacker (Iowa). Other derivatized cyclodextrins suitable in the invention include water soluble derivatized cyclodextrins. Exemplary water-soluble derivatized cyclodextrins include carboxylated derivatives; sulfated derivatives; alkylated derivatives; hydroxyalkylated derivatives; methylated derivatives; and carboxy-β-cyclodextrins, e.g. succinyl-β-cyclodextrin (SCD), and $6^A$-amino-$6^A$-deoxy-N-(3-carboxypropyl)-β-cyclodextrin. All of these materials can be made according to methods known in the prior art. Suitable derivatized cyclodextrins are disclosed in *Modified Cyclodextrins: Scaffolds and Templates for Supramolecular Chemistry* (Eds. Christopher J. Easton, Stephen F. Lincoln, Imperial College Press, London, UK, 1999) and *New Trends in Cyclodextrins and Derivatives* (Ed. Dominique Duchene, Editions de Santé, Paris, France, 1991).

The amount of derivatized cyclodextrin required to provide the desired effect in the formulation will vary according to the materials comprising the formulation. The amount of carrier that is useful in the composition of this invention is an amount that serves to uniformly distribute the active agent throughout the composition so that it can be uniformly dispersed when it is to be delivered to a subject in need thereof. It must also serve to dilute the active agent to a concentration at which the active agent can provide the desired beneficial palliative or curative results while at the same time minimizing any adverse side effects that might occur from too high a concentration. Thus, for an active agent that has high physiological activity, more of the carrier will be employed. On the other hand, for an active agent that exhibits a lower physiological activity a lesser quantity of the carrier will be employed. In general, the amount of carrier in the composition will be between about 50% wt. and 99.9% wt. of the total composition.

The formulation of the invention can be administered with any DPI device. Suitable devices include those that are commercially available such as, by way of example and without limitation, those sold under the trademark Aerohaler™ (Boehringer-Ingelhiem), Aerolizer™ (Novartis), Clickhaler™ (Innovata Biomed/ML laboratories Celitech), Cyclohaler™ (Pharmachemie), Diskhaler™ (GlaxoSmithKline), Diskus/Accuhaler™ (GlaxoSmithKline), Easyhaler™ (Orion Pharma), Pulvinal™ (Chiesi), Rotohalcr™ (GlaxoSmithKline), Spinhaler™ (Aventis), Acu-Breathe™ (Respirics, Inc), Nektar™ DPI (Nektar Therapeutics), Spiros™ DPI (Dura Pharmaceuticals, Inc), SkyeHaler™ (SkyePharma), or Oriel™ Powder Device (Oriel Therapeutics, Inc). Other suitable devices may not yet have been commercialized but are described in the scientific and/or patent literature.

DPI devices are available in formats with different Specific Resistance, $R_D$, (cmH$_2$O$^{0.5}$/L/min) to the flow of air and are often classified as: high 0.2 to 0.12 cmH$_2$O"/L/min, medium 0.12-0.07 cmH$_2$O$^{0.5}$/L/min, and low 0.07-0.03 cmH$_2$O$^{0.5}$/L/min pressure drop devices. The Rotahaler (GlaxoSmithKline), Spinhaler(Rhone Poulenc Rorer) Diskus, and Aerolizer have a low resistance, and the Diskhaler (GlaxoSmithKline), has a medium resistance; whereas the Inhalator, Clickhaler, Turbuhaler, Easyhaler (Orion Pharma) and the Twisthaler (Schering Plough) all have a high resistance.

Prior art formulations are generally suitable for use in only a few different DPI devices. For example, a particular lactose-containing formulation might be suitable for use in a high pressure drop device, but that formulation would not be suitable in a low pressure drop device. A study was conducted to determine the suitability of the present formulations for DPI range of devices having different pressure drops. Formulations containing lactose or SAE-CD, each containing sodium cromolyn, were made according to specific processes. The performance of the formulations was evaluated in low resistance (0.065 cmH$_2$O$^{0.5}$/L/min) and high resistance (0.18 cmH$_2$O$^{0.5}$/L/min) devices. The formulations described herein are suitable for use in any of such devices. The SAE-CD containing formulations were found to be suitable for delivery at low (15.2 g/cm$^2$ at 60 L/min) and high (54.4 g/cm$^2$ at 60 L/min) pressure drops which are equivalent to the Diskhaler and Inhalator (Handihaler) devices by delivering 25% fine particle fraction with an emitted dose in the 80-90% range. In contrast, lactose containing formulation was pressure drop dependent being substantially equivalent to the SAE-CD at high pressure drop but only delivering 15% FPF and 70% emitted dose at low pressure. The formulations of the invention are therefore capable of use in DPI devices in a substantially pressure drop independent manner.

For administration to the respiratory tract, particularly the lungs, a DPI device is used to deliver appropriately sized aggregates of particles of SAE-CD and active agent such that the aggregates dissociate for the most part into individual particles whereby the major portion of SAE-CD carrier is retained in the buccal cavity or throat and the major portion of active agent is delivered to the trachea or deeper into the respiratory tract.

Generally, decreasing the particle size of the carrier particles positively influences dispersion of active agent from SAE-CD. As noted in the dispersion study below, the fine particle fraction (stage 2 deposition in a twin stage impinger) from the smaller carrier particles was higher than for larger particles. The difference in particle size was determined according to the surface area of the SAE-CD batch used: the larger the surface area, the smaller the particle size. Increased fluidization (Stage 1+2 deposition) with larger carrier sizes was observed when using SAE-CD spray agglomerated powders: 175 to 270 μm median diameter), but this did not improve the fine particle fraction. In contrast, decreases in carrier particle size negatively influenced flow characteristics.

Intermediately dispersed powders (in terms of particle size) appear to possess optimal flow and dispersion properties; although, a degree of dispersity may help reduce inter-particulate interactions similarly to ternary blend mixtures. Intermediate sized carrier particles might be expected to prevent or reduce the direct interactions of drug and carrier particles. Therefore, monodisperse powders generally exhibit lower saturation of the carrier surface binding sites than polydisperse powders. However, polydisperse powders may also influence flow and dispersion properties of carrier systems negatively. Intercalation of smaller particles within larger particles will increase the effective contact area and inter-particulate interactions within the powder. Thus, carrier powder polydispersity is balanced between these competing influences.

Typically, the median particle diameter is between about 0.1 to 10 microns or about, 0.5 to about 6.4 microns. If it is desired that the particles reach the lower regions of the respiratory tract, i.e., the alveoli and terminal bronchi, the preferred median particle diameter size range is between about 0.5 and about 2.5 microns. If it is desired that the particles reach the upper respiratory tract, the preferred particle diameter size range is between 2.5 microns and 10 microns.

In one embodiment, the median diameter of the carrier particles lies between 50 and 1000 microns, or the median diameter of the carrier particles is less than 355 microns and lies between 60 and 250 microns, or between 90 and 250 microns. The relatively large diameter of the carrier particle improves the opportunity for active particles to become attached to carrier particles which is controlled by the above technique to provide good flow and entrainment characteristics and improved release of the active particles in the airways to increase deposition of the active particles in the lower lung.

The span (defined as the ratio=(particle size of the 90$^{th}$ percentile—particle size of 10$^{th}$ percentile)/median particle size) of the particle size distribution can also impact performance of the carrier. SAE-CD having broad, moderate and narrow particle size distribution may be used in the invention. Specific embodiments include those wherein the span is about 1.5 and 2.9.

Since particles are present as a distribution, the distribution can be monomodal, bimodal or polymodal.

The influence of particle shape on powder flow and dispersion properties is multifaceted. Generally, spheres, or particles with a high degree of rotational symmetry, are preferred to irregular shapes for good flow and dispersion characteristics. However, spherical particles may have increased inter-particulate forces that restrict flow when polydisperse powders are used.

Particles with a smooth surface are generally preferred over rough particles due to particle-particle interlocking and increases in frictional forces that occur with rough (non-smooth) particles. However, if surface asperities (protrusions) are in the appropriate dimensions, increases in separation distances between particles can lead to decreased inter-particulate forces and improved flow. If asperities are much larger than drug particle size, entrapment of active agent may occur thereby reducing dispersion of the active agent from the carrier during administration with a DPI device.

The morphology of SAE-CD particles can depend upon their method of preparation. Smooth (substantially smooth) surface particles can be prepared by spray drying, freeze drying a liquid or foam. Particles with a rough or substantially dented surface can be prepared by spray agglomeration.

| Parameter | Shape | | | Surface rugosity | |
| --- | --- | --- | --- | --- | --- |
| | Sphericity | Angularity | Elongation | Material surface | Particle appearance |
| Lactose Bulk | low | high | moderate | rough | Agglomerates |

-continued

| Parameter | Shape | | | Surface rugosity | |
| | Sphericity | Angularity | Elongation | Material surface | Particle appearance |
|---|---|---|---|---|---|
| Lactose | low | high | moderate | rough | Agglomerates |
| A | high | low | low | smooth | Indentations, soccer-ball |
| B | high | low | low | smooth | Agglomerates |
| C | high | low | low | smooth | Individual particles |
| D | high | low | low | smooth | Aggregates |
| E | Moderate | low | low | rough | Agglomerates |
| F | Moderate | low | low | rough | Agglomerates |
| G | low | high | moderate | smooth | Agglomerates |

"A" denotes SAE-CD prepared by spray drying using two-fluid nozzle atomization.
"B" denotes SAE-CD prepared by spray drying as per "A" followed by sieving of the particulate.
"C" denotes SAE-CD prepared by spray drying but with counter-current high pressure nozzle atomization.
"D" denotes SAE-CD prepared by spray drying with co-current high pressure nozzle atomization.
"E" denotes SAE-CD prepared by spray agglomeration at 25% wt./wt.
"F" denotes SAE-CD prepared by spray agglomeration at 50% wt./wt.
"G" denotes SAE-CD prepared by freeze drying of a frozen foam comprising SAE-CD and water.

In general, SAE-CD particles that are rougher unexpectedly provide increased powder flow in a DPI device.

Within each system tested, per the example below, for dispersion properties (i.e. drug-device and entrainment tube studies) increasing sphericity and particle size distribution decreased the fine particle fraction (deposition to stage 2 of liquid impinger). However, increasing sphericity also decreased drug deposition in the device and throat indicating that sphericity did not influence entrainment of the carrier particle to the extent that it influences drug detachment from the carrier surface. This indicates the powder was entrained via large aggregates rather than as a function of individual particle size. Thus, stage 1 deposition was increased as the carrier particles became more spherical and broadly distributed. Per the two dispersion studies below, SAE-CD carrier derived from a foam provides improved performance over SAE-CD carrier made according to other specific processes.

The SAE-CD containing particles can be provided as individual (not aggregates or agglomerates but otherwise still plural) particles, aggregates and agglomerates. Individual particles can be prepared by spray drying. Aggregated particles can be prepared by spray drying. Agglomerated particles can be prepared by spray agglomeration, spray drying or freeze-drying of a foam.

The bulk flow and microflow properties of SAE-CD solid were obtained according to the examples below. The Carr's Index ranged from 10-40% compressibility. The static angle of repose ranged from 28-45 degrees. The micro-flow properties had a fractal dimension analysis of about 1.00-1.31, preferred embodiments having a range of about 1.0-1.2.

Moisture content of the SAE-CD carrier can vary according to its method of preparation. Batches having a moisture content of less than about 3%, 6%, 8% or 10%, wt. have been prepared.

SAE-CD is a polyanionic material that generally possesses a negative electrostatic charge. The electrostatic charge of the SAE-CD carrier is generally about −1.4 to −3.7, 2 to −3.7, or 2 to −2 nC/g (nC is defined as nanocoulombs) when the material is processed and equilibrated as described herein. Prior to equilibration in a controlled atmosphere, the SAE-CD carrier can be obtained with an even more electronegative charge. By increasing the amount of moisture in the equilibration atmosphere, the electronegative charge of the SAE-CD carrier can be modified as needed.

The electrostatic charge of a blend (comprising active agent and SAE-CD carrier) will vary according to the electrostatic charge of the individual components, among other things. The table below depicts the electrostatic charge of some blends.

| Blend | Charge (nC/g) |
|---|---|
| "D" + Na-cromolyn | 1.48 |
| "F" + Na-cromolyn | −0.17 |
| "G" + Na-cromolyn | −0.24 |
| "D" + albuterol sulfate | 0.52 |
| "F" + albuterol sulfate | 4.04 |
| "G" + albuterol sulfate | −0.52 |
| "D" + Na-fluorescein | −0.64 |
| "F" + Na-fluorescein | −0.63 |
| "G" + Na-fluorescein | −0.27 |

The above should be read in view of the electrostatic charge of the corresponding drugs, the data for which is summarized in the table below.

| Electrostatic Charge Range | Approx. Magnitude (nC/g) | Exemplary Active Agent | Suggested Carrier Charge Range | Approx. Magnitude (nC/g) |
|---|---|---|---|---|
| Highly negative | <−3 | Na fluorescein | Neutral to low negative | 0 to −1 |
| Moderately negative | −3 to −2 | | | 0 to −1.5 |
| Low negative | −2 to −0.5 | Na Cromolyn | Low negative | −0.5 to −2 |
| Neutral | −0.5 to 0.5 | | Wide range | −2 to +2 |
| Low positive | 0.5 to 2 | | Low positive | 0.5 to 2 |
| Moderately positive | 2 to 4 | | | 0 to 1.5 |
| Highly positive | >4 | Albuterol | Neutral to low positive | 0 to 1 |

The table above sets forth approximate operating ranges for the suggested electrostatic charge of the SAE-CD carrier and the corresponding electrostatic charge of the active agent. In other words, the table should be read such that an active agent having a particular electrostatic charge is preferably formulated with an SAE-CD carrier having a particular electrostatic charge. For example, a highly negative or moderately negative drug is preferably formulated in a dry powder DPI device with SAE-CD carrier having a neutral to low negative electrostatic charge. In view of the above and other aspects discussed herein, it should be understood that an SAE-CD can serve as a suitable dry powder carrier for a full range of drugs differing in their electrostatic charges.

Dispersion studies according to the example below of albuterol from Captisol® and lactose blends indicate significant influence of electrostatic charge on the carrier systems. Dynamic electrostatic charge measurements showed that micronized albuterol carries a significant positive charge. Comparison between Captisol® and lactose as carrier particles showed that lactose systems (neutral charge) more efficiently delivered micronized drug to stage 2 (fine particles) than Captisol® systems (moderate to strong negative charge). Thus, without being held bound to a particular mechanism, it is postulated that SAE-CD carrier particles exhibit greater drug attachment than lactose when albuterol is used as the model drug system. The SAE-CD powder (derived from foam) with the smallest negative charge exhibited the most stage 2 deposition of albuterol.

The charge of the carrier particles was compared to dispersion performances from the entrainment tubes for albuterol and cromolyn. Charge neutral carrier particles resulted in significantly greater retention of drug (albuterol or cromolyn) in the entrainment tube. A similar correlation was obtained for Throat deposition. In addition, stage 1 deposition showed an inverse correlation where increasing the negative charge of the carrier resulted in a greater percentage of drug delivered to this stage. Correlations between drug dispersion to stage 2 and electrostatic charge were smaller. Albuterol stage 2 deposition was also related to the electrostatic charge of the carrier. However, the cromolyn (small negative charge) stage 2 deposition appeared to be less dependent on electrostatics.

Accordingly, the polarity and magnitude of charge of the carrier particles and model drugs significantly influences performance of the dry powder formulations. Albuterol (high positive charge), sodium cromolyn (electroneutral), and fluorescein (moderate negative charge) were dispersed more readily using either Lactose (electro-neutral, small size), or SAE-CD derived from foam (moderate negative charge, small size) as compared to spray dried or spray agglomerated SAE-CD carrier.

Electrostatic and morphological characteristics are factors involved in the good dispersion properties observed with SAE-CD carrier derived from foam. Those powder particles had smooth, angular surfaces and were generally minimally aggregated with a slight elongation of the particles. Together with a relatively lower electrostatic charge and small size, dispersion to Stage 2 of the liquid impinger was significantly higher than other SAE-CD based carrier systems.

SAE-CD (high negative charge, large size) fluidized albuterol well (entrainment tube experiments) and dispersed the drug well when a high-resistance (high turbulence) inhaler device was used (Inhalator™). The high inter-particulate forces between carrier and albuterol can be overcome using the Inhalator. This indicates that the fluidization of the SAE-CD powder (due to size and morphology) can be maximized by appropriate selection of device for lung delivery.

Mixing of carrier and micronized drug particles can influence the electrostatics of the system. Mixing may induce triboelectrification and increase electrostatic charge. Drug particle adhesion to carrier particle surface may result in charge shielding and reduce the electrostatics of the system. The electrostatics of the powder blends described above were determined and attempts were made to correlate these results with the dispersion performance observed in the liquid impinger studies. Increasing electrostatic charge of the blend has a beneficial effect on dispersion of the powder formulation from the entrainment tubes. Increasing the charge of the blend correlated with decreased device and throat deposition, while stage 1 deposition was increased. The differences in electrostatic charge of the blends may result from differences in adhesion between drug and carrier particles. Positively charged blends may result from more loosely bound micronized drug particles detaching from the carrier particles during electrostatic charge measurements (i.e. during powder flow). In addition, the positive charge of the blends may represent free micronized drug particles in the blend. This may result from saturation of binding sites on the SAE-CD carrier. In this case, the net electrostatic charge measured will be dominated by micronized drug particle charge (i.e. albuterol carries a positive charge). Conversely, blends with negative electrostatic charge may represent systems in which carrier-drug adhesion is dominant. Thus, in these cases the charge of the blend is a useful predictor of powder dispersion characteristics.

Figure 2:
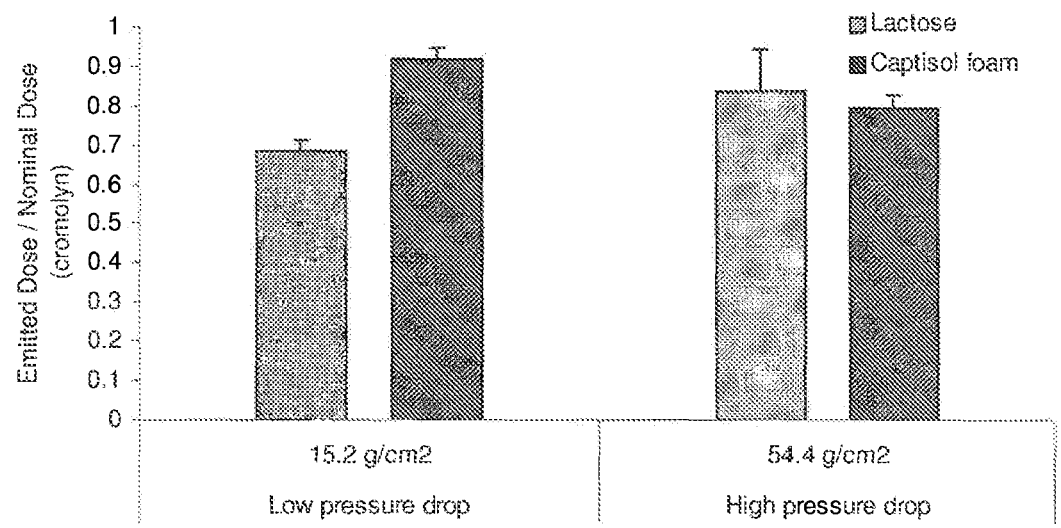
FIG. 2 depicts a chart of the emitted dose of cromolyn as a fraction of the nominal dose in low and high pressure devices (mean+SD) of FIG. 1.

As a result of the good dispersion performance of SAE-CD, derived from foam, in the entrainment tubes, a full dispersion study was performed in comparison with lactose using sodium cromolyn as the model drug in an eight-stage non-viable cascade impactor. The Inhalator™ device was used to provide maximum turbulence. The results indicate that, in this system, the dispersion properties of Lactose and SAE-CD were equivalent at high-pressure drop. However, the performance of SAE-CD derived from foam appears to be pressure drop independent (FIG. 1). Its performance is consistent for different devices (FPF means are not statistically different). In contrast, lactose dispersion performance appears to be significantly influenced by device characteristics (P=0.005).). Variability of the FPF also appears to be higher in the lactose formulation (FIG. 2)(P=0.027 for low pressure device variances, no significant difference for high pressure device variances). There was no significant difference ($\alpha=0.05$) in the variability of emitted doses for lactose and SAE-CD foam.

An overall evaluation of the impact of the physicochemical and morphological properties of SAE-CD upon performance as a dry powder carrier for DPI administration was conducted.

Albuterol

The model drug albuterol and the commercially available CAPTISOL™ were used. Albuterol is a highly positively charged powder when micronized for respiratory delivery. It has typical particle size and morphological characteristics for micronized drugs that are prepared for inhalation (size 1-5 µm, predominantly crystalline structure). The properties of the SAE-CD were matched with that of albuterol and the following results were obtained.

Size Selection:

Generally, decreasing the particle size of the carrier particles positively influences dispersion characteristics. In contrast, decreases in carrier particle size negatively influenced flow characteristics. Therefore, intermediate particle sizes that balance flow performance with dispersion characteristics are useful for DPI formulations. Lactose and SAE-CD particles derived from foam demonstrate these characteristics. The optimal median particle diameter for dispersion, which depends upon the nature of drug and carrier, can be between about 47 and 125 µm for the specific forms of albuterol and SAE-CD evaluated.

Polydispersity selection:

Particle size distribution also has an influence on powder flow and dispersion. Intermediately dispersed powders can have optimal flow and dispersion properties. Some degree of dispersity helps reduce inter-particulate interactions similarly to ternary blend mixtures. Intermediate sized carrier particles can prevent or reduce the direct interactions of drug and carrier particles. Therefore, monodisperse powders exhibit lower saturation of the carrier surface binding sites than polydisperse powders. However, polydisperse powders can influence flow and dispersion properties of carrier systems negatively. Intercalation of smaller particles within larger particles will increase the effective contact area and inter-particulate interactions within the powder. Thus, carrier powder polydispersity is balanced between these competing influences. Generally, particle size distributions for carrier particles, for optimal dispersion, should have moderate dispersity, i.e. particle size span should be between 1.5 and 2.9.

Morphology Selection:

The influence of particle shape on powder flow and dispersion properties is multifaceted. In the art, spheres or particles with a high degree of rotational symmetry are preferred over irregular shapes for good flow and dispersion characteristics. However, SAE-CD spherical particles may have increased inter-particulate forces that restrict flow when polydisperse powders are used. In the art and according to the invention, smooth particles are generally preferred over rough particles due to particle-particle interlocking and increases in frictional forces. However, if surface asperities are in the appropriate dimensions, increases in separation distances between particles can lead to decreased inter-particulate forces and improved flow. This was accomplished by using spray agglomerated Captisol® rather than foam derived Captisol®. If asperities are much larger than drug particle size entrapment may occur that reduces dispersion. Therefore, the smooth and irregular (i.e. not planar or geometric) morphology of the SAE-CD derived from foam is desirable for carrier particles with micronized drug particles, when compared to SAE-CD prepared by other processes.

Selection of Charge:

Electrostatic forces generally increase inter-particulate forces and reduce drug dispersion upon administration. SAE-CD derived from foam has relatively lower electrostatic charge than SAE-CD prepared by other methods, so that one can achieve significantly higher drug dispersion performance with albuterol using that particular form of SAE-CD. Electrostatic charge is known to be a function of moisture content (increasing moisture content decreases electrostatic charge), particle size (decreasing particle size generally increases electrostatic charge), surface area (increased charge obtained with increased surface area), and other physico-chemical properties (such as crystallinity and energy input) of the carrier and drug system. For albuterol, with highly positively charged particles, the charge of the carrier should be close to neutral. This is achieved by preparing SAE-CD according to the process described herein.

Cromolyn

The physicochemical and morphological properties of the SAE-CD carrier can be matched to those of other drugs as well. Micronized sodium cromolyn for inhalation has slightly negative electrostatic charge characteristics (−1 to −1.7 nC/g). Otherwise, it has typical particle size and morphological characteristics for micronized drugs that are prepared for inhalation (size 1-5 μm, predominantly crystalline structure).

Size and Polydispersity Selection:

Size and size distribution (polydispersity) selection for appropriate carrier particles for development of a dry powder inhaler system follow the same guidelines as discussed above for albuterol. Moderate particle size (between 45 and 125 μm) and distribution (particle size span should be between 1.5 and 2.9) characteristics are desirable. In addition, morphological features suitable for carrier particles are substantially the same as those described for albuterol: smooth, irregular surfaces (which properties are found in SAE-CD carrier prepared from dried foam).

Selection of Charge:

SAE-CD derived from dried foam had relatively lower charge characteristics that may contributed to the significantly higher drug dispersion performance of it with sodium cromolyn as compared to other SAE-CD carrier systems, such as those prepared by spray drying or spray agglomeration. However, further advantage was gained by using the SAE-CD derived from foam formulation is also better than lactose, which is relatively neutral. By matching the slightly negatively-charged drug particles with low negatively-charged SAE-CD carrier particles, a dry powder system that is flow independent was obtained, i.e. fine particle dose was independent of the pressure drop used to disperse the dry powder formulation. This is truly unexpected and is a direct result of the desired combination of physicochemical and morphological properties that can only be achieved with SAE-CD but not with lactose.

Accordingly, the median particle size, size distribution, morphology and electrostatic charge properties of SAE-CD are readily modified to match the wide variety of micronized drug characteristics that are presented to a formulator of the art. The ionic nature of SAE-CD facilitates the preparation of dry powder carriers of varying degrees of electrostatic charge, which are dependent upon the method of preparation and the chemical structure of the SAE-CD. Thus, a key advantage of the present invention over other cyclodextrin derivatives and lactose, in terms of its use as a carrier, is the ability of an artisan to modulate the physicochemical properties of the SAE-CD to match drug properties thereby resulting in an optimal dry powder formulation suitable for administration by DPI.

Drugs intended for inhalation therapy, carried out by the administration of dry powders, are characterized by a particle size of a few microns. The particle size is quantified by measuring a characteristic equivalent sphere diameter, known as aerodynamic diameter, which expresses the ability of the particles to be transported as a suspension in an air stream (aerosolization). In general, particles with an aerodynamic diameter of less than 10 microns or less than 6.4 microns are regarded as respirable, i.e. capable of penetrating into the lungs.

The dosage form of the invention can be used to administer a wide range of active agents by inhalation when administered with a DPI device. Active agents are suitable for endobronchial (intrapulmonary, intratracheal, intraaveolar) administration.

Corticosteroids that are useful in the present invention generally include any steroid produced by the adrenocortex, including glucocorticoids and mineralocorticoids, and synthetic analogs and derivatives of naturally occurring corticosteroids having anti-inflammatory activity. Suitable synthetic analogs include prodrugs, ester derivatives Examples of corticosteroids that can be used in the compositions of the invention include aldosterone, beclomethasone, betamethasone, butoxicart, budesonide, ciclesonide (Altana Pharma AG), cloprednol, cortisone, cortivazol, deoxycortone, desonide, desoximetasone, dexamethasone, difluorocortolone, fluclorolone, flumethasone, flunisolide, fluocinolone, fluocinonide, fluocortin butyl, fluorocortisone, fluorocortolone, fluorometholone, flurandrenolone, fluticasone, halcinonide, hydrocortisone, icomethasone, loteprednol, meprednisone, methylprednisolone, mometasone, paramethasone, prednisolone, prednisone, rofleponide, RPR 106541, tixocortol, triamcinolone, and their respective pharmaceutically acceptable derivatives, such as beclomethasone diproprionate, beclomethasone monoproprionate, dexamethasone 21-isonicotinate, fluticasone propionate, icomethasone enbutate, tixocortol 21-pivalate, and triamcinolone acetonide. Particularly preferred are compounds such as beclomethasone diproprionate, budesonide, flunisolide, fluticasone propionate, mometasone furoate, and triamcinolone acetonide.

Other specific active agents that can be employed according to the invention include pentamidine isethiouate, albuterol sulfate, metaproterenol sulfate, flunisolide, cromolyn sodium, sodium cromoglycate, ergotamine tartrate, levalbuterol, terbutaline, reproterol, salbutamol, salmeterol, formoterol, fenoterol, clenbuterol, bambuterol, tulobuterol, broxaterol, epinephrine, isoprenaline or hexoprenaline, an anticholinergic, such as tiotropium, ipratropium, oxitropium or glycopyrronium; a leukotriene antagonist, such as andolast, iralukast, pranlukast, imitrodast, seratrodast, zileuton, zafirlukast or montelukast; a phosphodiesterase inhibitor, such as filaminast or piclamilast; a paf inhibitor, such as apafant, forapafant or israpafant; a potassium channel opener, such as amiloride or furosemide; a painkiller, such as morphine, fentanyl, pentazocine, buprenorphine, pethidine, tilidine, methadone or heroin; a potency agent, such as sildenafil, alprostadil or phentolamine; a peptide or protein, such as insulin, erythropoietin, gonadotropin or vasopressin; calcitonin, factor ix, granulocyte colony stimulating factor, granulocyte macrophage colony, growth hormone, heparin, heparin (low molecular weight), interferon alpha, interferon beta, interferon gamma, interleukin-2, luteinizing hormone releasing hormone, somatostatin analog, amylin, ciliary neurotrophic factor, growth hormone releasing factor, insulin-like growth factor, insulinotropin, interleukin-1 receptor antagonist, interleukin-3, interleukin-4, interleukin-6, macrophage colony stimulating, factor (m-csf), nerve growth factor, parathyroid hormone, thymosin alpha 1; iib/iiia inhibitor, alpha-1 antitryp sin, anti-rsv antibody, cystic fibrosis transmembrane regulator (cftr) gene, deoxyribonuclease (dnase), bactericidal/permeability (ards), increasing protein anti-cmv antibody, interleukin-1 receptor, or a pharmaceutically acceptable derivative or salt of these compounds.

The weight of a unit dose of dry powder will vary according to the active agent present, its therapeutic activity, its toxicological profile, the amount at which it is present in the dry powder, and other factors known to the artisan. In general, the active agent is present at about 0.1% to about 50% wt. of the dry powder formulation, the balance being the carrier and optionally one or more other materials. The carrier comprises SAE-CD and optionally one or more other materials.

For the treatment of bronchial inflammation, the corticosteroid is preferably either beclomethasone dipropionate, betamethasone, budesonide, dexamethasone, flunisolide, fluticasone propionate, mometasone furoate, or triamcinolone acetonide, and is formulated in the concentrations set forth herein. The daily dose of the corticosteroid is generally about 0.05 to 10 mg, depending on the drug and the disease, in accordance with the Physician's Desk Reference.

The active agent can be present in its neutral, ionic, salt, basic, acidic, natural, synthetic, diastereomeric, epimeric, isomeric, enantiomerically pure, racemic, solvate, hydrate, chelate, derivative, analog, esterified, non-esterified, or other common form. Whenever an active agent is named herein, all such forms available are included.

The formulation of the invention can be used to deliver two or more different active agents. Particular combinations of active agents can be provided by the present formulation. Some combinations of active agents include: 1) a first drug from a first therapeutic class and a different second drug from the same therapeutic class; 2) a first drug from a first therapeutic class and a different second drug from a different therapeutic class; 3) a first drug having a first type of biological activity and a different second drug having about the same biological activity; 4) a first drug having a first type of biological activity and a different second drug having a different second type of biological activity. Exemplary combinations of active agents are described herein.

A corticosteroid, such as budesonide, can be administered in combination with one or more other drugs. Such other drugs include: $B_2$ adrenoreceptor agonist, $D_2$ receptor agonist, anticholinergic agent.

$B_2$-Adrenoreceptor agonists for use in combination with the compositions provided herein include, but are not limited to, Albuterol (alpha$^1$-(((1,1-dimethylethyl)amino) methyl)-4-hydroxy-1,3-benzenedimethanol); Bambuterol. (dimethylcarbamic acid 5-(2-((1,1-dimethylethyl)amino)-1-hydroxyethyl)-1,3-phenylene ester); Bitolterol (4-methylbenzoic acid 4-(2-((1,1-dimethylethyl)amino)-1-hydroxyethyl)-1,2-phenyleneester); Broxaterol (3-bromo-alpha-(((1,1-dimethylethyl)amino)methyl)-5-isoxazolemethanol); Isoproterenol (4-(1-hydroxy-2-((1-methylethyl-)amino) ethyl)-1,2-benzene-diol); Trimetoquinol (1,2,3,4-tetrahydro-1-((3,4-3,5-trimethoxyphenyl)-methyl)-6,7-isoquinolinediol); Clenbuterol (4-amino-3,5-dichloro-alpha-(((1,1-diemthylethyl)amino)methyl)benzenemethanol); Fenoterol (5-(1-hydroxy-2-((2-(4-hydroxyphenyl)-1-methylethyl)amino)ethyl)-1,3-benzenediol); Formoterol (2-hydroxy-5-((1RS)-1-hydroxy-2-(((1RS)-2-(p-methoxyphenyl)-1-methylethyl)amino)ethyl)formanilide); (R,R)-Formoterol; Desformoterol ((R,R) or (S,S)-3-amino-4-hydroxy-alpha-(((2-(4-methoxyphenyl)-1-methyl-ethyl)amino)methyl)benzenemethanol); Hexoprenaline (4,4'-(1,6-hexane-diyl)-bis (imino(1-hydroxy-2,1-ethanediyl)))bis-1,2-benzenediol); Isoetharine (4-(1-hydroxy-2-((1-meth-ylethyl)amino)butyl)-1,2-benzenediol); Isoprenaline (4-(1-hydroxy-2-((1-methylethyl)amino)ethyl)-1,2-benzenediol); Meta-proterenol (5-(1-hydroxy-2-((1-methylethyl)amino)ethyl)-1,3-benzenediol); Picumeterol (4-amino-3,5-dichloro-alpha-(((6-(2-(2-pyridinypethoxy)hexyl)-amino)methyl) benzenemethanol); Pirbuterol (.alpha.sup.6-(((1,1-dimethylethyl)-amino)methyl)-3-hydroxy-2,6-pyridinemethanol); Procaterol (((R*,S*)-(.+−.)-8-hydroxy-5-(1-hydroxy-2-((1-methylethyl)amino-)butyl)-2(1H)-quinolin-one); Reproterol ((7-(3-((2-(3,5-dihydroxyphenyl)-2-hydroxyethyl)amino)-propyl)-3,7-dihydro-1,3-dimethyl-1H-purine-2,6-dione)-; Rimiterol (4-(hydroxy-2-piperidinylmethyl)-1,2-benzenediol); Salbutamol ((.+−.)-alpha$^1$-(((1,1-dimethylethyl)amino)methyl)-4-hydroxy-1,3-b-enzenedimethanol); (R)-Salbutamol; Salmeterol (.+−.)-4-hydroxy-.alpha$^1$-(((6-(4-phenylbutoxy)hexyl)-amino) methyl)-1,3-benzenedimethanol); (R)-Salmeterol; Terbutaline (5-(2-((1,1-dimethylethyl)amino)-1-hydroxyethyl)-1,3-benzenediol); Tulobuterol (2-chloro-.alpha.-(((1,1-dimethylethyl)amino)methyl)benzenemethanol); and TA-2005 (8-hydroxy-5-((1R)-1-hydroxy-2-(N-((1R)-2-(4-methoxyphenyl)-1-methylethyl)amino)ethyl)carbostyril hydrochloride).

Dopamine ($D_2$) receptor agonists include, but are not limited to, Apomorphine ((r)-5,6,6a,7-tetrahydro-6-methyl-4H-dibenzo[de,g]quinoli-ne-10,11-diol); Bromocriptine ((5'.alpha.)-2-bromo-12'-hydroxy-2'-(1-methylethyl)-5'-(2-methylpropyl)ergotaman-3',6', 18-trione); Cabergoline ((8.beta.)-N-(3-(dimethylamino)propyl)-N-((ethylamino) carbonyl)-6-(2-propenyl)ergoline-8-carboxamide); Lisuride (N'-((8-alpha-)-9,10-di-dehydro-6-methylergolin-8-yl)-N, N-diethylurea); Pergolide ((8-beta-)-8-((methylthio) methyl)-6-propylergoline); Levodopa (3-hydroxy-L-tryrosine); Pramipexole ((s)-4,5,6,7-tetrahydro-N.sup.6-prop-yl- 2,6-benzothiazolediamine); Quinpirole hydrochirodie (trans-(−)-4-aR-4,4-a,5,6,7,8,8a,9-octahydro-5-propyl-1H-pyrazolo[3,4-g]qui-noline hydrochloride); Ropinirole (4-(2-(dipropylamino)ethyl)-1,3-dihydro-2H-indol-2-one); and Talipexole (5,6,7,8-tetrahydro-6-(2-propenyl)-4H-thia-zolo[4,5-d]azepin-2-amine). Other dopamine $D_2$ receptor agonists for use herein are disclosed in International Patent Application Publication No. WO 99/36095.

Anticholinergic agents for use herein include, but are not limited to, ipratropium bromide, oxitropium bromide, atropine methyl nitrate, atropine sulfate, ipratropium, belladonna extract, scopolamine, scopolamine methobromide, homatropine methobromide, hyoscyamine, ispriopramide, orphenadrine, benzalkonium chloride, tiotropium bromide and glycopyrronium bromide. In certain embodiments, the compositions contain an anticholinergic agent, such as ipratropium bromide or tiotropium bromide, at a concentration of about 5 μg,/mL to about 5 mg/mL, or about 50 μg/mL, to about 200 μg/mL. In other embodiments, the compositions for use in the methods herein contain an anticholinergic agent, including ipratropium bromide and tiotropium bromide, at a concentration of about 83 μg/mL or about 167 μg/ml.

Other active ingredients for use herein in combination therapy, include, but are not limited to, IL-5 inhibitors such as those disclosed in U.S. Pat. Nos. 5,668,110, 5,683,983, 5,677,280 and 5,654,276; antisense modulators of IL-S such as those disclosed in U.S. Pat. No. 6,136,603; milrinone (1,6-dihydro-2-methyl-6-oxo-[3,4'-bipyridine]-5-carb-onitrile); milrinone lactate; tryptase inhibitors such as those disclosed in U.S. Pat. No. 5,525,623; tachykinin receptor antagonists such as those disclosed in U.S. Pat. Nos. 5,691,336, 5,877,191, 5,929,094, 5,750,549 and 5,780,467; leukotriene receptor antagonists such as montelukast sodium (Singular®, R-(E)]-1-[([[1-[3-[2-(7-chloro-2-quinolinyl)ethenyl]-phenyl]-3-[2-(1-hydroxy-1-methylethyl)phenyl]-propyl]thio]methyl]cyclopro-paneacetic acid, monosodium salt), 5-lypoxygenase inhibitors such as zileuton (Zyflo™, Abbott Laboratories, Abbott Park, Ill.), and anti-IgE antibodies such as Xolair™ (recombinant humanized anti-IgE monoclonal antibody (CGP 51901; IGE 025A; rhuMAb-E25), Genentech, Inc., South San Francisco, Calif.).

The invention includes methods for treatment, prevention, or amelioration of one or more symptoms of bronchoconstrictive disorders. The method further includes administering one or more of (a), (b), (c) or (d) as follows: (a) a $b_2$-adrenoreceptor agonist; (b) a dopamine ($D_2$) receptor agonist; (c) a prophylactic therapeutic, such as a steroid; or (d) an anticholinergic agent; simultaneously with, prior to or subsequent to the composition provided herein.

The bronchoconstrictive disorder to be treated, prevented, or whose one or more symptoms are to be ameliorated is associated with asthma, including, but not limited to, bronchial asthma, allergic asthma and intrinsic asthma, e.g., late asthma and airway hyper-responsiveness; and, particularly in embodiments where an anticholinergic agent is used, other chronic obstructive pulmonary diseases (COPDs), including, but not limited to, chronic bronchitis, emphysema, and associated cor pulmonale (heart disease secondary to disease of the lungs and respiratory system) with pulmonary hypertension, right ventricular hypertrophy and right heart failure. COPD is frequently associated with cigarette smoking, infections, environmental pollution and occupational dust exposure.

Other disorders and diseases than can be treated by administration of a unit dose of active agent via a DPI device according to the invention include Osteoporosis Prophylaxis, Paget's Disease, Hypercalcemia, Anemia, Hemophilia, Neutropenia, Bone Marrow Engraft/Transplant Failure, Short stature, Renal Failure, Blood Clotting, Type I and Type II Diabetes, Hepatitis B and C, Hairy Cell Leukemia, Kaposi's Sarcoma, Multiple Sclerosis, Chronic Granulomatous Disease, Renal Cancer, Prostate Cancer, Endometriosis, Gastrointestinal Cancers, Diabetes Insipidus, Bed Wetting, Lou Gehrig's Disease, Osteoporosis, Nutritional Support, Rheumatoid Arthritus, Adjuvant to Chemotherapy, Immunodeficiency Disease, Thrombocytopenia, Fungal Disease, Cancer, Hypercholesterolemia, Peripheral Neuropathies, Refractory Diarrheas, Unstable Angina, Cystic Fibrosis, Respiratory Syncytial Virus, Chronic Bronchitus, Asthma, Adult Respiratory Distress Syndrome, Cytomegalovirus, pneumocystis carini pneumonia, Broncospasm, Bronchial asthma, or Migraine.

Even though SAE-CD can be the sole carrier in a dry powder formulation according to the invention, it is possible to add other carriers to the formulation to further improve its performance. Such other carriers include lactose (in any of its known forms suitable for DPI administration), and any of the standard carbohydrate and amino acid carriers that are known in the art to be useful excipients for inhalation therapy, either alone or in combination. These excipients are generally relatively free-flowing particulate solids, do not thicken or polymerize upon contact with water, are toxicologically innocuous when inhaled as a dispersed powder and do not significantly interact with the active agent in a manner that adversely affects the desired physiological action of the agent. Carbohydrate excipients that are particularly useful in this regard include the mono- and polysaccharides. Representative monosaccharides include carbohydrate excipients such as dextrose (anhydrous and the monohydrate; also referred to as glucose and glucose monohydrate), galactose, mannitol, D-mannose, sorbitol, sorbose and the like. Monosaccharides are readily publicly available; for example, dextrose is available from companies such as Mallinckrodt, Inc., Corn Products Co., CPC (UK) Ltd., and/or others. Mannitol and sorbitol are available from companies such as ICI Americas, Inc., McKesson Chemical Co., Merck & Co., Atlas Chemical Industries (UK) Ltd., and/or others. Representative disaccharides, such as lactose, maltose, sucrose, trehalose and the like, can be obtained from companies such as McKesson Chemical Co., Aldrich Chemical Co., Inc., Great Western Sugar Co., and/or others. Representative trisaccharides include those such as raffinose and the like that are readily available from commercial sources.

Suitable amino acid carriers include any of the naturally occurring amino acids that form a powder under standard pharmaceutical processing techniques and include the nonpolar (hydrophobic) amino acids and polar (uncharged, positively charged and negatively charged) amino acids, such amino acids are of pharmaceutical grade and are generally regarded as safe (GRAS) by the U.S. Food and Drug Administration. Representative examples of non-polar amino acids include alanine, isoleucine, leucine, methionine, phenylalanine, proline, tryptophan and valine. Representative examples of polar, uncharged amino acids include cystine, glycine, glutamine, serine, threonine, and tyrosine. Representative examples of polar, positively charged amino acids include arginine, histidine and lysine. Representative examples of negatively charged amino acids include aspartic acid and glutamic acid. Of these, glycine is preferred. These amino acids are generally available from commercial sources that provide pharmaceutical-grade products such as the Aldrich Chemical Company, Inc., Milwaukee, Wis. or Sigma Chemical Company, St. Louis, Mo.

Although not necessary, the formulation of the present invention may include a antioxidant, acidifying agent, alkalizing agent, buffering agent, solubility-enhancing agent, penetration enhancer, electrolyte, fragrance, glucose, glidant, stabilizer, bulking agent, cryoprotectant, plasticizer, flavors, sweeteners, surface tension modifier, density modifier, volatility modifier, other excipients known by those of ordinary skill in the art for use in preserved formulations, or a combination thereof. Upon each occurrence, these materials can be independently included in the active agent-containing particles or the carrier particles. For example, the carrier might include one or more of these materials and the active agent-containing particles might also include one or more of these materials.

As used herein, the term "glidant" is intended to mean an agent used to promote flowability of the dry powder. Such compounds include, by way of example and without limitation, magnesium stearate, sodium dodecylsulfate, colloidal silica, cornstarch, talc, calcium silicate, magnesium silicate, colloidal silicon, silicon hydrogel and other materials known to one of ordinary skill in the art.

As used herein, the term "antioxidant" is intended to mean an agent that inhibits oxidation and thus is used to prevent the deterioration of preparations by the oxidative process. Such compounds include, by way of example and without limitation, acetone, potassium metabisulfite, potassium sulfite, ascorbic acid, ascorbyl palmitate, citric acid, butylated hydroxyanisole, butylated hydroxytoluene, hypophosphorous acid, monothioglycerol, propyl gallate, sodium ascorbate, sodium citrate, sodium sulfide, sodium sulfite, sodium bisulfite, sodium formaldehyde sulfoxylate, thioglycolic acid, EDTA, pentetate, and sodium metabisulfite and others known to those of ordinary skill in the art.

As used herein, the term "alkalizing agent" is intended to mean a compound used to provide alkaline medium when the dry powder of the invention is exposed to water. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, diethanolamine, organic amine base, alkaline amino acids and trolamine and others known to those of ordinary skill in the art.

As used herein, the term "acidifying agent" is intended to mean a compound used to provide an acidic medium when the dry powder of the invention is exposed to water. Such compounds include, by way of example and without limitation, acetic acid, acidic amino acids, citric acid, fumaric acid and other alpha hydroxy acids, hydrochloric acid, ascorbic acid, phosphoric acid, sulfuric acid, tartaric acid and nitric acid and others known to those of ordinary skill in the art.

As used herein, the term "buffering agent" is intended to mean a compound used to resist change in pH upon exposure to a medium of a different pH. Buffers are used in the present compositions to adjust the pH to a range of between about 2 and about 8, about 3 to about 7, or about 4 to about 5. By controlling the pH of the dry powder, irritation to the respiratory tract can be minimized. Such compounds include, by way of example and without limitation, acetic acid, sodium acetate, adipic acid, benzoic acid, sodium benzoate, boric acid, sodium borate, citric acid, glycine, maleic acid, monobasic sodium phosphate, dibasic sodium phosphate, HEPES, lactic acid, tartaric acid, potassium metaphosphate, potassium phosphate, monobasic sodium acetate, sodium bicarbonate, tris, sodium tartrate and sodium citrate anhydrous and dihydrate and others known to those of ordinary skill in the art. Other buffers include citric acid/phosphate mixture, acetate, barbital, borate, Britton-Robinson, cacodylate, citrate, collidine, formate, maleate, McIlvaine, phosphate, Prideaux-Ward, succinate, citrate-phosphate-borate (Teorell-Stanhagen), veronal acetate, MES (2-(N-morpholino)ethanesulfonic acid), BIS-TRIS (bis(2-hydroxyethyl)imino-tris(hydroxymethyl)methane), ADA (N-(2-acetamido)-2-iminodiacetic acid), ACES (N-(carbamoylmethyl)-2-aminoethanesulfonaic acid), PIPES (piperazine-N,N-bis(2-ethanesulfonic acid)), MOPS (3-(N-morpholino)-2-hydroxypropanesulfonic acid), BIS-TRIS PROPANE (1,3-bis(tris(hydroxymethyl)methylamino)propane), BES (N,N-bis(2-hydroxyethyl)-2-aminoethanesulfonaic acid), MOPS (3-(N-morpholino)propanesulfonic acid), TES (N-tris(hydroxymethyl)methyl-2-aminoethanesulfonic acid), HEPES (N-(2-hydroxyethyl)piperazine-N'-(2-ethanesulfonic acid), DIPSO (3-(N,N-bis(2-hydroxyethyl)amino)-2-hydroxypropanesulfonic acid), MOBS (4-(N-morpholino)-butanesulfonic acid), TAPSO (3-(N-tris (hydroxymethyl)methylamino)-2-hydroxypropanesulfonic acid), TRIZMA™ (tris(hydroxymethylaminomethane), HEPPSO (N-(2-hydroxyethyl)piperazine-N'-(2-hydroxypropanesulfonic acid), POPSO (piperazine-N,N'-bis(2-hydroxypropanesulfonic acid)), TEA (triethanolamine), EPPS (N-(2-hydroxyethyl)piperazine-N'-(3-propanesulfonic acid), TRICINE (N-tris(hydroxymethyl)-methylglycine), GLY-GLY (glycylglycine), BICINE (N,N-bis(2-hydroxyethyl)glycine), HEPBS (N-(2-hydroxyethyl)piperazine-N'-(4-butanesulfonic acid)), TAPS(N-tris(hydroxymethyl) methyl-3-aminopropanesulfonic acid), AMPD (2-amino-2-methyl-1,3-propanediol), and/or any other buffers known to those of skill in the art.

Hydrophilic polymers can be used to improve the performance of formulations containing a cyclodextrin. Loftsson has disclosed a number of polymers suitable for combined use with a cyclodextrin (underivatized or derivatized) to enhance the performance and/or properties of the cyclodextrin. Suitable polymers are disclosed in *Pharmazie* (2001), 56(9), 746-747; *International Journal of Pharmaceutics* (2001), 212(1), 29-40; Cyclodextrin: From Basic Research to Market, International Cyclodextrin Symposium, 10th, Ann Arbor, Mich., United States, May 21-24, 2000 (2000), 10-15 (Wacker Biochem Corp.: Adrian, Mich.); PCT International Publication No. WO 9942111; *Pharmazie*, 53(11), 733-740 (1998); *Pharm. Technol. Eur.,* 9(5), 26-34 (1997); *J. Pharm. Sci.* 85(10), 1017-1025 (1996); European Patent Application EP0579435; Proceedings of the International Symposium on Cyclodextrins, 9th, Santiago de Comostela, Spain, May 31-Jun. 3, 1998 (1999), 261-264 (Editor(s): Labandeira, J. J. Torres; Vila-Jato, J. L. Kluwer Academic Publishers, Dordrecht, Neth); *S.T.P. Pharma Sciences* (1999), 9(3), 237-242; ACS Symposium Series (1999), 737(Polysaccharide Applications), 24-45; *Pharmaceutical Research* (1998), 15(11), 1696-1701; *Drug Development and Industrial Pharmacy* (1998), 24(4), 365-370; *International Journal of Pharmaceutics* (1998), 163(1-2), 115-121; Book of Abstracts, 216th ACS National Meeting, Boston, Aug. 23-27 (1998), CELL-016, American Chemical Society; *Journal of Controlled Release*, (1997), 44/1 (95-99); *Pharm. Res.* (1997) 14(11), S203; *Investigative Ophthalmology & Visual Science*, (1996), 37(6), 1199-1203; Proceedings of the International Symposium on Controlled Release of Bioactive Materials (1996), 23rd, 453-454; *Drug Development and Industrial Pharmacy* (1996), 22(5), 401-405; Proceedings of the International Symposium on Cyclodextrins, 8th, Budapest, Mar. 31-Apr. 2, (1996), 373-376. (Editor(s): Szejtli, J.; Szente, L. Kluwer: Dordrecht, Neth.); *Pharmaceuti-* cal Sciences (1996), 2(6), 277-279; European Journal of Pharmaceutical Sciences, (1996), 4(SUPPL.), S144; Third European Congress of Pharmaceutical Sciences Edinburgh, Scotland, UK Sep. 15-17, 1996; Pharmazie, (1996), 51(1), 39-42; Eur. J. Pharm. Sci. (1996), 4(Suppl.), S143; U.S. Pat. No. 5,472,954 and No. 5,324,718; International Journal of Pharmaceutics (Netherlands), (Dec. 29, 1995) 126, 73-78; Abstracts of Papers of the American Chemical Society, (02 APR 1995) 209(1), 33-CELL; Eurbpean Journal of Pharmaceutical Sciences, (1994) 2, 297-301; Pharmaceutical Research (New York), (1994) 11(10), S225; International Journal of Pharmaceutics (Netherlands), (Apr. 11, 1994) 104, 181-184; and International Journal of Pharmaceutics (1994), 110(2), 169-77, the entire disclosures of which are hereby incorporated by reference.

Other suitable polymers are well-known excipients commonly used in the field of pharmaceutical formulations and are included in, for example, Remington's Pharmaceutical Sciences, 18th Edition, Alfonso R. Gennaro (editor), Mack Publishing Company, Easton, Pa., 1990, pp. 291-294; Alfred Martin, James Swarbrick and Arthur Commarata, Physical Pharmacy. Physical Chemical Principles in Pharmaceutical Sciences, 3rd edition (Lea & Febinger, Philadelphia, Pa., 1983, pp. 592-638); A. T. Florence and D. Altwood, (Physicochemical Principles of Pharmacy, 2nd Edition, MacMillan Press, London, 1988, pp. 281-334. The entire disclosures of the references cited herein are hereby incorporated by references. Still other suitable polymers include water-soluble natural polymers, water-soluble semi-synthetic polymers (such as the water-soluble derivatives of cellulose) and water-soluble synthetic polymers. The natural polymers include polysaccharides such as inulin, pectin, algin derivatives (e.g. sodium alginate) and agar, and polypeptides such as casein and gelatin. The semi-synthetic polymers include cellulose derivatives such as methylcellulose, hydroxyethylcellulosc, hydroxypropyl cellulose, their mixed ethers such as hydroxypropyl methylcellulose and other mixed ethers such as hydroxyethyl ethylcellulose and hydroxypropyl ethylcellulose, hydroxypropyl methylcellulose phthalate and carboxymethylcellulose and its salts, especially sodium carboxymethylcellulose. The synthetic polymers include polyoxyethylene derivatives (polyethylene glycols) and polyvinyl derivatives (polyvinyl alcohol, polyvinylpyrrolidone and polystyrene sulfonate) and various copolymers of acrylic acid (e.g. carbomer). Other natural, semi-synthetic and synthetic polymers not named here which meet the criteria of water solubility, pharmaceutical acceptability and pharmacological inactivity are likewise considered to be within the ambit of the present invention.

A solubility-enhancing agent can be added to the dry powder formulation of the invention. A solubility-enhancing agent is a compound, or compounds, that enhance(s) the solubility of active agent in an aqueous or moist environment, such as the lining of respiratory tract. Suitable solubility enhancing agents include one or more organic solvents, detergents, soaps, surfactants and other organic compounds typically used in parenteral formulations to enhance the solubility of a particular agent. Suitable organic solvents include, for example, ethanol, glycerin, poly(ethylene glycols), propylene glycol, poly(propylene glycols), poloxomers, and others known to those of ordinary skill in the art.

As used herein, the term "cryoprotectant" is intended to mean a compound used to protect an active agent from physical or chemical degradation during lyophilization. Such compounds include, by way of example and without limitation, dimethyl sulfoxide, glycerol, trehalose, propylene glycol, polyethylene glycol, and others known to those of ordinary skill in the art.

Plasticizers can also be included in the preparations of the invention to modify the properties and characteristics thereof. As used herein, the term "plasticizer" includes all compounds capable of plasticizing or softening a polymer or binder used in invention. The plasticizer should be able to lower the melting temperature or glass transition temperature (softening point temperature) of the polymer or binder. Plasticizers, such as low molecular weight PEG, generally broaden the average molecular weight of a polymer in which they are included thereby lowering its glass transition temperature or softening point. Plasticizers also generally reduce the viscosity of a polymer. It is possible the plasticizer will impart some particularly advantageous physical properties to the osmotic device of the invention.

Plasticizers useful in the invention can include, by way of example and without limitation, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, low molecular weight poly(ethylene glycol), citrate ester-type plasticizers, triacetin, propylene glycol and glycerin. Such plasticizers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. All such plasticizers are commercially available from sources such as Aldrich or Sigma Chemical Co. It is also contemplated and within the scope of the invention, that a combination of plasticizers may be used in the present formulation. The PEG based plasticizers are available commercially or can be made by a variety of, methods, such as disclosed in Poly (ethylene glycol) Chemistry: Biotechnical and Biomedical Applications (J. M. Harris, Ed.; Plenum Press, NY) the disclosure of which is hereby incorporated by reference.

As used herein, the term "flavor" is intended to mean a compound used to impart a pleasant flavor and often odor to a pharmaceutical preparation. Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors which have been found to be particularly useful include commercially available orange, grape, cherry and bubble gum flavors and mixtures thereof. The amount of flavoring may depend on a number of factors, including the organoleptic effect desired. Flavors will be present in any amount as desired by those of ordinary skill in the art. Particularly flavors are the grape and cherry flavors and citrus flavors such as orange.

As used herein, the term "sweetener" is intended to mean a compound used to impart sweetness to a preparation. Such compounds include, by way of example and without limitation, aspartame, dextrose, glycerin, mannitol, saccharin sodium, sorbitol, fructose, high fructose corn syrup, maltodextrin, sucralose, sucrose, other materials known to one of ordinary skill in the art, and combinations thereof.

As used herein, a penetration enhancer is an agent or combination of agents that enhances penetration of an active agent through tissue. Penetration enhancers which can be included in the present formulation include, by way of example and without limitation, calcium chelators such as EDTA, methylated β-cyclodextrin, and polycarboxylic acids; surfactants such as sodium lauryl sulfate, sodium dodecyl sulfate, carnitine, carnitine esters, and tween; bile salts such as sodium taurocholate; fatty acids such as oleic and linoleic acid; and non-surfactants such as AZONE™ and dialkyl sulfoxides; E-flux inhibitors such as AV171 (AyMax, Inc., South San Francisco, Calif.), D-α-tocopheryl polyethylene glycol 1000 succinate (TPGS), and peppermint oil; chitosan and chitosan derivatives such as N-methyl chitosan, N-trimethyl chitosan, mono-N-carboxymethyl chitosan, quaternized chitosan derivatives; SNAC(N-(8-[2-hydroxybenzoyl]amino) caprylate) and SNAD (N-[10-(2-hydroxybenzoyl)amino]-decanoate) (Emisphere Technologies, Inc., Tarrytown, N.Y.); N-acylated non-alpha amino acids; HEMISPHERE brand delivery agents; Gélucire 44/14 or Vitamin E TPGS; CARBOPOL® 934P; others known to those of ordinary skill in the art; and combinations thereof.

As used herein, a fragrance is a relatively volatile substance or combination of substances that produces a detectable aroma, odor or scent. Exemplary fragrances include those generally accepted as FD&C.

A "surface tension modifier" is a material or combination of materials capable of modifying the surface properties of a composition according to the invention. A surface tension modifier can include a surfactant, detergent or soap. It can be included in the carrier particles, the active agent-containing particles or both.

A "density modifier" is a material or combination of materials that is included in a composition of the invention to increase or decrease the density thereof. It can be included in the carrier particles, the active agent-containing particles or both. A density modifier can be used to increase or decrease (as needed) the density of the carrier in order enhance dispersion of the active agent from the carrier. Likewise, a density modifier can be used to decrease or increase, respectively, (as needed) the density of the active agent containing particles.

A "volatility modifier" is a material or combination of materials added to modify the volatility of an active agent. In one embodiment, the volatility modifier increases the volatility of the active agent. In another, embodiment, the volatility modifier decreases the volatility of the active agent.

As used herein, the term "stabilizer" is intended to mean a compound used to stabilize the therapeutic agent against physical, chemical, or biochemical process that would reduce the therapeutic activity of the agent. Suitable stabilizers include, by way of example and without limitation, albumin, sialic acid, creatinine, glycine and other amino acids, niacinamide, sodium acetyltryptophonate, zinc oxide, sucrose, glucose, lactose, sorbitol, mannitol, glycerol, polyethylene glycols, sodium caprylate and sodium saccharin and other known to those of ordinary skill in the art.

As used herein, the term "bulking agent" is intended to mean a compound used to add bulk to the lyophilized product and/or assist in the control of the properties of the formulation during lyophilization. Such compounds include, by way of example and without limitation, dextran, trehalose, sucrose, polyvinylpyrrolidone, lactose, inositol, sorbitol, dimethylsulfoxide, glycerol, albumin, calcium lactobionate, and others known to those of ordinary skill in the art.

It should be understood that compounds used in the art of pharmaceutical formulations generally serve a variety of functions or purposes. Thus, if a compound named herein is mentioned only once or is used to define more than one term herein, its purpose or function should not be construed as being limited solely to that named purpose(s) or function(s).

An active agent contained within the present formulation can be present as its pharmaceutically acceptable salt. As used herein, "pharmaceutically acceptable salt" refers to derivatives of the disclosed compounds wherein the active agent is modified by reacting it with an acid or base as needed to form an ionically bound pair. Examples of pharmaceutically acceptable salts include conventional non-toxic salts or the quaternary ammonium salts of the parent compound formed, for example, from non-toxic inorganic or organic acids. Suitable non-toxic salts include those derived from inorganic acids such as hydrochloric, hydrobromic, sulfuric, sulfonic, sulfamic, phosphoric, nitric and others known to those of ordinary skill in the art. The salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonie, ethane disulfonic, oxalic, isethionic, and others known to those of ordinary skill in the art. The pharmaceutically acceptable salts of the present invention can be synthesized from the parent active agent which contains a basic or acidic moiety by conventional chemical methods. Lists of other suitable salts are found in *Remington's Pharmaceutical Sciences*, 17$^{th}$. ed., Mack Publishing Company, Easton, Pa., 1985, the relevant disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "patient" or "subject" are taken to mean warm blooded animals such as mammals, for example, cats, dogs, mice, guinea pigs, horses, bovine cows, sheep and humans.

A formulation of the invention will comprise an active agent present in an effective amount. By the term "effective amount", is meant the amount or quantity of active agent that is sufficient to elicit the required or desired response, or in other words, the amount that is sufficient to elicit an appreciable biological response when administered to a subject.

In view of the above description and the examples below, one of ordinary skill in the art will be able to practice the invention as claimed without undue experimentation. The foregoing will be better understood with reference to the following examples that detail certain procedures for the preparation of formulations according to the present invention. All references made to these examples are for the purposes of illustration. The following examples should not be considered exhaustive, but merely illustrative of only a few of the many embodiments contemplated by the present invention.

EXAMPLE 1

Exemplary formulations according to the invention were made according to the following general procedures.

Method A

A solid composition comprising cyclodextrin is mixed with a solid composition comprising active agent until homogeneity. The materials are kept in a climate-controlled environment to minimize exposure thereof to excessive moisture. The cyclodextrin-containing and active agent-containing compositions contain less than about 10% wt. water. The process is preferably, but optionally, conducted under an anhydrous or substantially anhydrous (less than 30%, 20% or 10% R.H.) atmosphere. Mixing of the two compositions can also include simultaneous attritting thereof or attrition can be performed as a separate process step. For example, the cyclodextrin-containing composition and the active agent-containing compositions are each attritted separately prior to mixing. Following completion of mixing, the dry powder formulation is optionally partitioned into individual DPI device reservoirs, which are then sealed. The process can be conducted in a vacuum or under positive pressure.

Method B

A particulate carrier comprising cyclodextrin is attritted and optionally screened (sieved) to the desired particle size distribution. A particulate composition comprising active agent is attritted and optionally screened to the desired particle size range. The two resulting materials are mixed in a solids mixer until homogeneity to optimize association of carrier and active agent-containing particles to form a dry powder according to the invention. The dry powder is then charged into plural individual DPI device reservoirs, which are then sealed. The process is conducted under a substantially anhydrous atmosphere and optionally with an inert gas purge.

Method C

Lactose and Captisol® (SAE-CD; SBE7-β-CD) blends were prepared in 1 g batches, each containing 2% w/w micronized drug. A pre-blend was prepared using geometric dilution by mixing the drug and carrier in glass vial with a small spatula. The pre-blend was mixed using a Turbula mixer (Glen Mills, N.J.). The pre-blends were mixed at the maximum rotation speed for 10 minutes. The homogeneity of the blends was examined using random samples (5×20 mg) removed from each blend. The drug content of each sample was determined using UV analysis. The mean drug content, standard deviation and coefficient of variation was determined.

EXAMPLE 2

Preparation of SAE-CD-containing carrier.

Method A

An SAE-CD carrier is derived from a foam as follows. A solution of SAE-CD in water is provided and an inert gas is optionally bubbled through the solution. The solution should have a viscosity thick enough to permit formation of a foam. In general, SAE-CD is present at a concentration of about 10% to 80% wt./wt., or 20% to 75% wt./wt. or 30% to 65% wt./wt. The solution is placed in a freezing apparatus equipped with an agitator. (An exemplary apparatus is the ELECTROFREEZE Model 30TN-CAD-132.) As the foam mixture is agitated, it is gradually frozen in the apparatus to form a frozen foam. The frozen foam is then dehydrated, such as by freeze-drying (lyophilizing), to form a friable porous material, which is attritted to provide a carrier having a suitable particle size range.

Method B

An SAE-CD carrier is prepared by spray agglomeration in an FSD-16 fluid spray drier apparatus as follows. Several solutions of Captisol® at 20.1-49.8% solids were agglomerated in the FSD-16 using a Spraying Systems pressure nozzle at atomization pressures of 1,500-2,000 psig. Process conditions were inlet/outlet temperatures of 210-250/83-100° C., fluid bed inlet temperatures of 80-100° C., and fluid product bed temperatures of 67-87° C. Fines return at the nozzle and at the chamber cone was investigated during separate runs. The drying gas flows are heated electrically.

Feed solutions containing SAE-CD were prepared by adding powdered constituents to the required amount of water under heat and agitation in the feed tank. Final feed formulations has viscosities of about 11-32 cps.

Typical FSD agglomerates were obtained during all runs. Product was analyzed to have median sizes of 175-277 microns, residual volatiles (moisture) of 3.17-5.19%, and bulk densities of 0.34-0.55 g/cc.

Method C

SAE-CD carrier is prepared from foam by the following alternate procedure. An aqueous solution containing SAE-CD (30% wt./wt.) is purged with nitrogen and processed in an ELECTROFRFEZE™ 30TN-CAD-132 combination freezer/agitator to provide a frozen foam. The foam is then lyophilized to form a friable porous particulate glass. The particulate material is passed through a 40-mesh screen. The material that is retained by the screen is attritted in a TURBULAT™ tumble mixer until all of it passes through the 40-mesh screen. This material had a moisture content of 3.4% and an electrostatic charge of about −6.5 nC/g. It was then equilibrated at 30% R.H. for about 24 hours at ambient temperature to reduce the electrostatic to about −2.5 nC/g.

Method D

SAE-CD carrier is prepared from foam by the following alternate procedure. An aqueous solution containing SAE-CD, and optionally one or more other materials, is processed in a drum dryer (such as from BUFLOVAK LLC, Buffalo, N.Y.) having at least one heated drum. As the solution is poured onto the drum under vacuum, the solution turns into foam from which water evaporates leaving behind a brittle foam (or flake) having a low moisture content (less than 10% wt). The foam is then removed from the surface of the drum by scraping. The dried foam is then attritted as detailed herein to the desired particle size range. The vacuum drum dryer can be a single or double drum dryer. It must have at least one internally heated drum. Depending upon the construction of the dryer used, it can be operated in a batch, semi-continuous or continuous mode. The weight percentage of SAE-CD in the feed solution can be modified as desired to provide the desired solution viscosity, process performance or product qualities. Changing the viscosity of the feed solution can vary the thickness of the foam layer. A water soluble organic solvent, such as alcohol or ether, is optionally added to the feed solution. A water insoluble material is optionally included in the feed solution. Prior to evaporation of the water, the SAE-CD solution is optionally degassed by exposure to vacuum and/or treatment with an inert gas. By "degassed" is meant the concentration of air or gas present in the solution is reduced.

EXAMPLE 3

Determination of the particle size distribution of the dry powder formulation, the active agent-containing formulation and the SAE-CD-containing carrier.

The particle size distributions of lactose, maltodextrin and Captisol® were determined by laser diffraction (Malvern, 2600c, Malvern, UK), using the dry powder feeder attachment (Malvern, PS 40, Malvern, UK), running at 15 psi. The powder was sampled using 500 detector sweeps for statistical validity. The obscuration values were monitored to ensure adequate data acquisition. The 300 mm focal length detector lens was used, providing a size range of 5.8 to 564 mm. Other laser diffraction particle size measurements were performed by Cyclex using a Horiba instrument.

The particle size analysis for an exemplary SAE-CD carrier prepared according to Method A of Example 2 is included in the table below.

| Seive Size (μm) | Weight of Sample in Seive (g) | % of total sample weight | Cumulative % Under Size |
|---|---|---|---|
| 250 | 0.2895 | 14.06 | 85.94 |
| 180 | 0.1769 | 8.592 | 77.35 |
| 106 | 0.3016 | 14.65 | 62.70 |
| 90 | 0.1259 | 6.115 | 56.59 |
| 75 | 0.1155 | 5.610 | 50.98 |
| 45 | 0.3857 | 18.73 | 32.24 |
| 0 | 0.6639 | 32.24 | 0.00 |

EXAMPLE 4

Determination of the moisture content of the dry powder formulation, the active agent-containing formulation and the SAE-CD-containing carrier. The moisture content was measured via the Karl Fisher or moisture balance methods.

Moisture Balance

A Mettler Toledo LJ16 moisture balance (Mettler Toledo, Columbus Ohio) was used to determine the weight loss of selected powder samples over time as the powder was exposed to infrared heating. The powders were weighed (approximately 1 g for each sample), and the following heating program was performed: 105° C. for 30 minutes. At the end of this program the percentage weight loss was calculated.

EXAMPLE 5

Determination of the morphology (such as surface rugosity) of the SAE-CD-containing carrier.

Surface morphology of carrier particles was determined visually by scanning electron microscopy (SEM). Samples were adhered onto sample stubs using double-sided tape, palladium/gold-coated and viewed using a ten kilovolt (kV) potential difference.

EXAMPLE 6

Determination of the flow and micro-flow properties of the SAE-CD-containing carrier. The flowability of the powder systems was measured using both static and dynamic means (Carr's compressibility index, static angle of repose, vibrating spatula—strain gauge experiments, and rotating drum).

Static Angle of Repose

A funnel was placed in a ring stand and set to a height so that the bottom of the funnel was 2 inches above a piece of graph paper. The funnel was filled with powder while plugging the bottom of the funnel. The powder was released and the base and height of the resulting pyramid was measured. The following formula was used to determine the static angle of repose:

$$\alpha = \tan^{-1}\left(\frac{h}{0.5*b}\right)$$

where α is the angle of repose, h is the height of the pyramid and b is the diameter of the base.

Carr's Compressibility Index

Bulk density was determined by pouring the powder into a 10 mL graduated cylinder. Record the volume and the weight of the powder to determine the mass/unit volume (g/mL). To determine the tapped density, a graduated cylinder was dropped through a height of 1 inch every 2 seconds onto a wooden surface until the height of the powder does not change. The volume and the weight of the powders was used to determine the mass/unit volume (g/mL). The data were represented in terms of Carr's compressibility index:

Vibrating Spatula

A vibrating spatula method was used to determine the dynamic flow characteristics of the powders during higher energy flow conditions than those during rotating drum experiments.

The vibrating spatula apparatus is a powder flow measurement device, constructed to acquire mass versus time profiles for powder flowing. Powder flowed from the vibrating spatula (Mettler LV3, MettlerToledo, Columbus Ohio) onto a powder collection surface, causing deflection and a change in resistance in semiconductor strain gauges (Micron Instruments, Simi Valley Calif.) mounted above and below the collection surface. After amplification (BP-3629, Burr Brown, Tucson Ariz.) of the differential voltage, the mass data was sampled by a PC data acquisition module (DI-170, Dataq Instruments, Akron Ohio). The data collection rate was user selectable in the range of 1-400 Hz. The filter control and the subsequent analysis of the stride length were controlled by a graphical user interface (GUI) written in the Matlab (The Mathworks, Natick Mass.) environment (higuchigui.m).

The temporal fractal dimension routine used a modification to Higuchi's method of determining the fractal dimension of a time series. The routine stepped iteratively through the flow profile calculating the length of the curve using stride lengths ranging from one data point at a time up to half the number of data points in the curve. The fractal dimension was determined by a linear least-squares regression method from the slope of the linear part of the Richardson plot, where the logarithm of the curve length was graphed as a function of the logarithm of stride length. The fractal dimension was calculated using three replicates of powder flow series for each powder sample. The fractal dimension was taken as the average of three different fractal dimension determinations. The three determinations were taken using the beginning and end points of flow, the beginning to middle and middle to end. This approach was used in order to reduce the effect of any particularly irregular portions of the data series.

Rotating Drum

A Micromeritics rotating drum instrument was used to analyze the powder flow characteristics during dynamic conditions. A 30 ml sample (sample size is by volume) of Captisol® (Lot#02047) was placed in the drum holder and the drum rotation speed was 2 revolutions per minute. Quantitative analysis was not performed as flow patterns could not be fitted to the algorithm.

EXAMPLE 7

Determination of the Electrostatic Charge of the SAE-CD-Containing Carrier and the Active agent-containing composition.

Electrostatic charge measurements were performed using a Faraday Cage apparatus that determines the potential difference changes as a function of time during powder flow onto a conducting surface. Samples were weighed and transferred from original containers to wax coated weighing papers. These were mounted to a vibrating spatula (set at maximum vibration level). The angle of the spatula was set at a constant angle (30 degrees). Powder was dispensed to the Faraday cage that was connected to a electrometer. Data collection was performed using Windaq interface and a PC computer sampling at 240 Hz. The area under the electrostatic dissipation curve was determined (Voltage×time) and charge (nC/g) was calculated from the known resistance of the setup.

EXAMPLE 8

Determination of the dispersion (disassociation) of the SAE-CD-containing carrier from the active agent-containing composition. The dispersion of drug from the model carrier systems was evaluated using several systems (standardized entrainment tube and inhaler devices) with either a twin stage liquid impinger or an eight stage non-viable cascade impactor.

Twin-stage Liquid Impinger Studies

The in vitro aerosol dispersion of albuterol blends in lactose and Captisol® were determined using a liquid impinger device. An airflow rate of 60 L/min, measured at the mouthpiece prior to impaction, was employed for 5 seconds. The inhaler devices used for dispersion studies were the Rotahaler (GlaxoSmithKline, RTP) and Inhalator (Boehinger Ingelheim, Germany). The powders were loaded into hard gelatin capsules in 20 mg doses.

Cascade Impaction

The in vitro aerosol dispersion efficiency was determined using an eight stage, non-viable cascade impactor (Graseby-Andersen, GA). An airflow rate of 60 L/min, measured at the mouthpiece prior to impaction, was employed for 10 seconds following actuation of the inhaler device. The theoretical aerodynamic cut-off diameters for each stage at 60 L/min are displayed in the table below.

| Cascade Impactor Stage | Theoretical Aerodynamic Cut-off Diameter (µm) |
| --- | --- |
| −1 | 8.6 |
| −0 | 6.2 |
| 1 | 4.0 |
| 2 | 3.2 |
| 3 | 2.3 |
| 4 | 1.4 |
| 5 | 0.8 |
| 6 | 0.5 |

Each impaction plate was pre-coated with a 1% w/v solution of silicon fluid in hexane and allowed to dry prior to impaction. The preseparator contained 10 mL of distilled water. Following impaction, the inhaler, throat and preseparator, each impaction plate and stages were rinsed with distilled water. The rinsing liquid was collected and the drug content was determined (n=3). The temperature and relative humidity of the surrounding environment was measured prior to each impaction. The inhaler devices used for dispersion studies were the Rotahaler (Glaxo Wellcome, RTP, NC) and Inhalator (Boehinger Ingelheim, Germany). Formulations were examine using 2% w/w drug in carrier blends. The powders were loaded into hard gelatin capsules (size 3, Eli Lily and Co., IN) in 20 mg powder doses.

The recovered dose (RD) was defined as the total mass of drug particles collected. The emitted dose (ED) was defined as the mass of particles delivered from the inhaler expressed as a percentage of the RD. The fine particle mass (FPM) was defined as the mass of dispersed particles smaller than 4 µm aerodynamic diameter (particles deposited in stage 2 and lower). The fine particle fraction (FPF) was defined as the mass of dispersed particles smaller than 4 µm aerodynamic diameter (particles deposited in stage 2 and lower), expressed as a percentage of the RD. The mass median aerodynamic diameter (MMAD) was calculated as the $50^{th}$ percentile of the aerodynamic particle size distribution by mass. The geometric standard deviation (GSD) was calculated as the ratio of the particle size at the $84^{th}$ percentile to the $50^{th}$ percentile, assuming a lognormal distribution. The MMAD and GSD were determined from the linear region of the plot (between the $16^{th}$ and $84^{th}$ percentile) of the cumulative mass distribution as a function of the logarithm of aerodynamic diameter using an Excel template. Linear regression was performed using a least-squares regression method.

EXAMPLE 9

Materials used for comparative evaluations: Lactose monohydrate was used in various forms: Bulk powder as received, sieved fractions 45-75 µm, 75-125 µm. Lactose monohydrate (Mallinckrodt NF, non-spray dried; Lot number 6270 KVMK) was used. A size fraction of 45 to 75 µm was prepared using a sieve shaker (Vibratory 3-Inch Sieve Shaker, Model SS-5, Gilson Company Inc., Worthington, Ohio). A powder loading of 30 g was placed on top of the sieves and tap mode was employed for 2 hours. Multiple sieving runs were combined and mixed.

A single maltodextrin (Maltrin QD 500M, Grain Processing Corporation, Lot number M9424790) was employed.

EXAMPLE 10

Evaluation of various blends of SAE-CD and active agent with dpi devices.

Dispersion studies were performed from three different dispersion devices: Rotahalor, Inhalator, and controlled flow/pressure drop standardized entrainment tubes. The inhaler devices used for dispersion studies were the Rotahaler (Glaxo Wellcome, RTP) and the Inhalator (Boehringer-Ingelheim). The powders were loaded into hard gelatin capsules in 20 mg doses. The devices used were examples of a low resistance inhaler (Rotahaler) and a high resistance inhaler (Inhalator) as shown in the table below.

TABLE

Comparison of the pressure drop measured in common DPI devices

| Device | Calculated Pressure Drop (g/cm$^3$) | |
|---|---|---|
| | 28.3 L/min | 60 L/min |
| Rotahaler | 1.04 | 4.67 |
| Inhalator | 12.12 | 54.46 |
| Entrainment Tube | 3.38 | 15.21 |

EXAMPLE 11

Differential scanning calorimetry was performed using a Perkin Elmer DSC 6. Samples tested were from a Captisol® spray dried batch (Lot# CY 3A 02047). The samples were hermitically sealed in aluminum pans (sample weight between 5-10 mg). The heating program was as follows:
1. Hold for 1.0 min at 80.00 deg centigrade.
2. Heat from 80 deg C. to 300 deg C. at 30 deg C./min
3. Return to load temperature The peak temperature, peak area, and enthalpy were calculated using the PE Pyris software.

EXAMPLE 12

Surface area analysis was performed using a multi-point BET on a Micromeritics (Norcross, Ga.) surface analyzer. The purge gas used was: 70/30 nitrogen/helium mixture or Krypton. Samples were degassed for at least 30 minutes.

EXAMPLE 13

Bulk density was determined by pouring the powder into a 10 mL graduated cylinder. Record the volume and the weight of the powder to determine the mass/unit volume (g/mL). To determine the tapped density, a graduated cylinder was dropped through a height of 1 inch every 2 seconds onto a wooden surface until the height of the powder does not change. The volume and the weight of the powders was used to determine the mass/unit volume (g/mL). The data were represented in terms of Carr's compressibility index:

$$\% \text{ compressibility} = \left(\frac{\text{Tap Density} - \text{Bulk Density}}{\text{Tap Density}}\right) \times 100\%$$

EXAMPLE 14

A spectrofluorometric or a UV/vis assay was employed for determination of albuterol sulfate. Standard and sample solutions were prepared using distilled water as the solvent. The fluorescence absorbance (Luminescense Spectrometer, Perkin Elmer, Norwalk, Conn.) was measured at an excitation wavelength ($\lambda_{ex}$) of 230 nm and emission wavelength ($\lambda_{em}$) of 310 nm. A slit width of 2.5 nm was employed for both excitation and emission. A quartz silica cuvette (1 cm path length) was employed. The UV absorbance was measured at an absorbance wavelength of 230 nm. A linear calibration curve was obtained ($r^2 > 0.99$).

EXAMPLE 15

A dry powder formulation suitable for administration with a DPI device comprises one or more active agents, SAE-CD carrier made according to Example 2 (Method A), and optionally one or more excipients selected from the group consisting of an antioxidant, acidifying agent, alkalizing agent, buffering agent, solubility-enhancing agent, penetration enhancer, electrolyte, fragrance, glucose, glidant, stabilizer, bulking agent, cryoprotectant, plasticizer, flavors, sweeteners, surface tension modifier, density modifier, volatility modifier, or a combination thereof. The following parameters are noted.
1—The one or more excipients are included in the carrier composition or in the active agent composition.
2—The SAE-CD carrier comprises an SAE-CD compound of the Formula 1 or a mixture thereof.
3—The SAE-CD carrier is derived from an SAE-CD foam.
4—The SAE-CD carrier has a median particle diameter in the range of 37 to 125 microns.
5—The active agent composition has a median particle diameter of less than 37 microns or in the range of about 10 microns or less.
6—The carrier has a moisture content of less than 10% wt.
7—The carrier has an electrostatic charge of −1.4 to −3.7 nC/g.
8—The carrier has a substantially smooth surface; although, it can comprise some asperities.
9—The carrier particles have been passed through a 420 micron sieve.

EXAMPLE 16

A dry powder formulation suitable for administration with a DPI device comprises one or more active agents, SAE-CD carrier comprising SAE-CD selected from the group consisting of SME-β-CD, SEE-β-CD, SPE-β-CD, SBE-β-CD, SPtE-β-CD, SHE-β-CD, SME-α-CD, SEE-α-CD, SPE-α-CD, SBE-α-CD, SPtE-α-CD, SHE-α-CD, SME-γ-CD, SEE-γ-CD, SPE-γ-CD, SBE-γ-CD, SPtE-γ-CD, and SHE-γ-CD and optionally one or more excipients selected from the group consisting of an antioxidant, acidifying agent, alkalizing agent, buffering agent, solubility-enhancing agent, penetration enhancer, electrolyte, fragrance, glucose, glidant, stabilizer, bulking agent, cryoprotectant, plasticizer, flavors, sweeteners, surface tension modifier, density modifier, volatility modifier, or a combination thereof. The SAE-CD carrier comprises about 50%-99.9% wt. of the formulation, and it has a median particle size of less than 420 microns. The active agent-containing particles have a median particle diameter between about 0.1 to 10 microns.

The carrier has a span of about 1.5 to 2.9, and the carrier has been made by forming a foam, dehydrating the foam to form a solid, and attritting the solid to form the particulate carrier. The SAE-CD used in the carrier has an average DS in the range of about 1 to 12.

EXAMPLE 17

A dry powder formulation suitable for administration with a DPI device comprises: a first particulate powdered active agent-containing composition comprising one or more active agents; and a second particulate powdered carrier composition comprising SAE-CD and optionally one or more excipients, wherein the first and second particulate compositions are homogeneously mixed. The carrier composition comprises about 50%-99.9% wt. of the formulation, and it has a median particle size of less than 420 microns. The active agent-containing composition has a median particle diameter between about 0.1 to 10 microns. The carrier has a span of about 1.5 to 2.9. The first particulate composition has an electrostatic charge more negative than about −2 nC/g, and the second particulate composition has an electrostatic charge in the range of about 0 to −1.5

EXAMPLE 18

A dry powder formulation suitable for administration with a DPI device is made according to Example 17, with the following exception. The first particulate composition has an electrostatic charge in the range of about −2 to −0.5 nC/g, and the second particulate composition has an electrostatic charge in the range of about −0.5 to −2.

EXAMPLE 19

A dry powder formulation suitable for administration with a DPI device is made according to Example 17, with the following exception. The first particulate composition has an electrostatic charge in the range of about 0.5 to −0.5 nC/g, and the second particulate composition has an electrostatic charge in the range of about −2 to 2.

EXAMPLE 20

A dry powder particulate carrier composition, which comprises an SAE-CD of the Formula 1 or Formula 2 and optionally one or more excipients, is made according to the invention to possess the following properties:
  a) a median particle diameter of less than 420 microns, and/or a median particle diameter in the range of about 37 to 125 or about 10 to 300 microns;
  b) a span of about 1.5 to 2.9;
  c) an electrostatic charge of −1.4 to −3.7 nC/g or 2 to −3.7 nC/g;
  d) a Carr's Index of about 10% to 40% compressibility;
  e) a static angle of repose from about 28 to 45 degrees;
  f) a fractal dimension analysis of about 1.00 to 1.31; and
  g) a moisture content of 10% wt. or less.
The following terms are defined as detailed below.

| TERM | DEFINITION |
|---|---|
| Adhesion, Adhesive forces | Adhesion and adhesive forces refer to interactions between particles of different materials. |
| Agglomerate | A collection of particles that are fused together and act as a larger particle. |
| Aggregate | Collection of particles that are gathered together but are not chemically bound or fused together. |
| Angle of repose | Angle between powder surface and horizontal plane measured after heaping |
| BET | Brunauer, Emmett, and Teller derived expression for the Type II adsorption isotherm that is used to calculate surface area materials |
| Bulk density | Mass of bulk powder divided by the bulk volume |
| Carr's Index | Measure of the bulk flow properties of powders. See description and equation on pages 39-40 |
| CD | Cyclodextrin |
| CFC | Chlorofluorocarbon propellant |
| Cohesion, Cohesive forces | Cohesion refers to interactions between particles of the same material |
| Deaggregation | The process by which aggregates (see aggregate) are disrupted into smaller particles or collection of particles |
| Dispersion | Term used to describe the generation of fine particles that are available for inhalation |
| DPI | Dry powder inhaler |
| DSC | Differential scanning calorimetry |
| Eight stage cascade impactor | Aerodynamic particle sizing instrument |
| Emitted dose | The mass of drug that is emitted from the device, i.e. recovered dose less the mass recovered from the device |
| Entrainment | See fluidization |
| Fine particle mass | See fine particle dose, FPD. |
| Fluidization | Refers to a fluid-solid interaction where solid particles are lifted and agitated by a stream of fluid (typically gas). At lower end of fluidization, solid particles behave like a boiling liquid. At the other extreme, particles are fully suspended in the fluid stream and are carried along with it (entrainment). |
| FPD | Fine particle dose, the mass of drug recovered from aerodynamic particle sizing methods that have particle sizes less than 6.4 μm (liquid impinger studies) or 5 μm (cascade impaction studies) |
| FPF | Fine particle fraction, fraction of the emitted dose that is below 6.4 μm (liquid impinger studies) or 5 μm (cascade impaction studies) |
| FPM | Fine particle mass |
| Fractal dimension | Relates to a property of an object to the scale of measurement. Microflow is quantified by fractal dimension. |
| GSD | Geometric standard deviation, used to describe the distribution width when a log-normal distribution is fitted to particle size data. It is a dimensionless quantity with values greater than 1. |
| HFA | Hydrofluoroalkane propellant |
| Inhaler resistance | The air flow resistance of a dry powder inhaler. Related to the smallest orifice size within the geometry of the inhaler and is also proportional to shear forces and turbulence. |
| KF | Karl Fisher Analysis |
| LD | Laser diffraction |
| MDI | Metered dose inhaler, or more correctly, propellant driven metered dose inhaler |
| Microflow | Powder flow on scales smaller than that of bulk flow. |
| MMAD | Mass median aerodynamic diameter is the median of the distribution that represents aerodynamic diameters on the basis of mass. |
| monodisperse | In terms of particle size, refers to a population of particles that have a uniform particle size |
| nC | nanoCoulomb, measure of charge |
| ND | Not determined |
| pMDI | pressurized metered dose inhaler |
| Poly-dispersity | In terms of particle size, refers to a population of particles that have wide range of particle sizes |
| Recovered dose (RD) | The dose mass of drug recovered from aerodynamic particle sizing experiment |
| Respirable | Typically an indication of the particles in the "respirable range" or that are in an aerodynamic particle size range that potentially will result in deposition in the peripheral regions of the lung |

-continued

| TERM | DEFINITION |
| --- | --- |
| | (1-5 μm). Note: In vitro aerodynamic particle size results do not necessarily infer that particles will or will not be respirable. |
| Rugosity | A qualitative description of the surface roughness of a particle or material surface. |
| SA | Spray aggregated (when referring to a type of SAE-CD powder), or Surface area |
| SD | Standard deviation |
| SEM | Scanning electron microscope |
| spheronization | The process by which materials are made spherical |
| Tapped density | Mass of bulk powder divided by the volume of packed powder (following compaction of the powder by vertical tapping) |
| Ternary blends/ components | Used in investigative studies for DPI formulations where the interactions between drug and carrier particles is modified (usually reduced) by the addition of a third component (typically fine particle size) |
| triboelec- trication | The generation of electrical charge by rubbing and frictional forces during motion of materials |
| Turbulent flow | When fluid flows slowly and smoothly, the flow is called laminar. At fast velocities, the inertia of the fluid overcomes fluid frictional forces and turbulent flow results. When a fluid is flowing this way it flows in eddies and whorls (vortices). When a fluid flows turbulently, there is much more drag than when the flow is laminar. |
| Twin stage liquid impinger | Aerodynamic particle sizing instrument |

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

The invention claimed is:

1. A composition comprising agglomerated particles comprising sulfoalkyl ether cyclodextrin, wherein the composition comprises less than 10% by weight moisture and has a property of a bulk density of 0.34 g/cc to 0.55 g/cc, a CARR's index of about 10% to about 40%, a median particle diameter of about 10 microns to about 300 microns, and wherein the agglomerated particles have a rough surface.

2. The composition of claim 1, wherein the sulfoalkyl ether cyclodextrin is a compound, or a mixture of compounds, of the Formula 1:

Formula 1

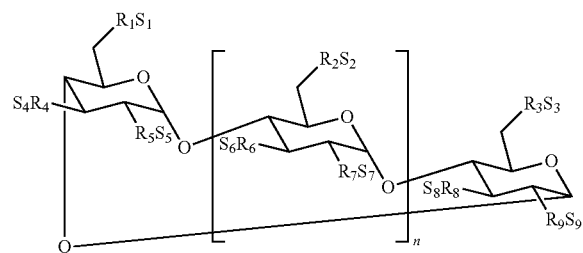

wherein:

n is 4, 5, or 6;

$R_1$, $R_2$, $R_3$, $R_4$, $R_5$, $R_6$, $R_7$, $R_8$, and $R_9$ are each, independently, $O^-$ or a $O$—$(C_{2-6}$ alkylene)-$SO_3^-$ group, wherein at least one of $R_1$ to $R_9$ is independently a $O$—$(C_2$-$C_6$ alkylene)-$SO_3^-$ group; and $S_1$, $S_2$, $S_3$, $S_4$, $S_5$, $S_6$, $S_7$, $S_8$, and $S_9$, are each, independently, a pharmaceutically acceptable cation selected from the group consisting of $H^+$, alkali metals, alkaline earth metals, ammonium ions and amine cations.

3. The composition of claim 1, wherein the composition comprises particles with a median particle diameter of about 175 microns to about 277 microns.

4. The composition of claim 1, wherein the composition comprises particles with a median particle diameter of about 37 microns to about 125 microns.

5. The composition of claim 1, wherein the composition comprises a particle size distribution span of about 1.5 to about 2.9.

6. The composition of claim 1, wherein the composition comprises a moisture content of less than 8% by weight.

7. The composition of claim 1, wherein the composition comprises a moisture content of less than 2.5% by weight.

8. The composition of claim 1, wherein the composition comprises a moisture content of less than 1% by weight.

9. The composition of claim 1, wherein the composition further comprises an excipient selected from the group consisting of an antioxidant, acidifying agent, alkalizing agent, buffering agent, solubility-enhancing agent, penetration enhancer, electrolyte, fragrance, glucose, glidant, stabilizer, bulking agent, cryoprotectant, plasticizer, flavor, sweetener, surface tension modifier, density modifier, volatility modifier, hydrophilic polymer, water soluble polymer, and combinations thereof.

10. The composition of claim 1, wherein the composition comprises a moisture content of 3.17-5.19% by weight.

11. The composition of claim 1 prepared by a process comprising a spray agglomeration of a feed solution using a spray drier apparatus to form agglomerated particles.

12. The composition of claim 11, wherein the spray drier apparatus comprises a pressure nozzle; an inlet; an outlet; a fluid bed inlet; and a fluid product bed.

13. The composition of claim 1, prepared by a process comprising:

(a) providing a liquid feed comprising a liquid carrier and SAE-CD;

(b) forming a fluidized bed of particles comprising SAE-CD in a drying chamber of a fluidized bed spray dryer apparatus;

(c) removing fine particles from the fluidized bed and returning them back into the drying chamber;

(d) atomizing liquid feed into the drying chamber: conducting larger particles to a second chamber containing a fluidized bed of particles; and (f) collecting particulate composition to provide the composition comprising SAE-CD.

14. The composition of claim 13, wherein the process further comprises removing fine particles from the second chamber and returning them to the drying chamber.

* * * * *